(12) United States Patent
Bluestone et al.

(10) Patent No.: US 7,722,862 B2
(45) Date of Patent: *May 25, 2010

(54) REGULATORY T CELLS SUPPRESS AUTOIMMUNITY

(75) Inventors: Jeffrey A. Bluestone, San Francisco, CA (US); Qizhi Tang, San Francisco, CA (US); Emma Masteller, San Francisco, CA (US)

(73) Assignee: The Regents of the University of California, Oakland, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 11/473,959

(22) Filed: Jun. 22, 2006

(65) Prior Publication Data

US 2006/0233751 A1    Oct. 19, 2006

(51) Int. Cl.
    *A01N 63/00*     (2006.01)
    *C12N 5/071*     (2010.01)
(52) U.S. Cl. .................. 424/93.71; 435/372.3
(58) Field of Classification Search ........................ None
See application file for complete search history.

(56) References Cited

U.S. PATENT DOCUMENTS

| | | | |
|---|---|---|---|
| 5,827,642 | A | 10/1998 | Riddell et al. |
| 6,316,257 | B1 | 11/2001 | Flyer et al. |
| 6,534,055 | B1 | 3/2003 | June et al. |
| 6,797,267 | B2 | 9/2004 | Horwitz |
| 6,803,036 | B1 | 10/2004 | Horwitz |
| 6,867,041 | B2 | 3/2005 | Berenson et al. |
| 2002/0019048 | A1 | 2/2002 | Berenson et al. |
| 2002/0058019 | A1 | 5/2002 | Berenson et al. |
| 2002/0119568 | A1 | 8/2002 | Berenson et al. |
| 2003/0082806 | A1 | 5/2003 | Berenson et al. |
| 2003/0119185 | A1 | 6/2003 | Berenson et al. |
| 2003/0124122 | A1 | 7/2003 | Berenson et al. |
| 2003/0147865 | A1 | 8/2003 | Salomon et al. |
| 2005/0003431 | A1 | 1/2005 | Wucherpfennig et al. |
| 2005/0101012 | A1 | 5/2005 | Schuler et al. |

FOREIGN PATENT DOCUMENTS

| | | | |
|---|---|---|---|
| WO | WO 03/028441 A1 | | 4/2003 |
| WO | WO 03066072 A2 * | | 8/2003 |

OTHER PUBLICATIONS

McGraw-Hill Dictionary of Scientific and Technical Terms, Definition of "multimer", 2003, pp. 1-2.*
Mukherjee et al., 2003, J. Autoimmunity, vol. 21: 221-237.*
Lin et al., 2003, Eur. J. Immunol. vol. 33: 626-638.*
Medline Medical Encyclopedia entry for "Type 1 diabetes", 2005, pp. 1-7.*
Janeway and Travers, 1997, Immunobiology, pp. 4:4-4:6 and 7:12.*
Levine et al., 1997, J. Immunol. vol. 159: 5921-5930.*
Takahashi et al., 1998, Int. immunol. vol. 10: 1969-1980.*
Davila, E., et al. "Cell-Based Immunotherapy with Suppressor CD8+ T Cells in Rheumatoid Arthritis[1]", J. Immunol., 2005, vol. 174 pp. 7292-7301.
Dieckmann, D., et al. "Ex Vivo Isolation and Characterization of CD4[30] CD25+ T Cells with Regulatory Properties from Human Blood." J. Exp. Med., Jun. 4, 2001, vol. 193, No. 11, pp. 1303-1310.
Lan, R., et al. "Regulatory T cells: Development, function and role in autoimmunity," Autoimmunity Reviews, 2005, vol. 4, pp. 351-363.
Levings, M., et al. "Human CD25+ CD4+ T Regulatory Cells Suppress Naive and Memory T Cell Proliferation and Can be Expanded in Vitro without Loss of Function." J. Exp. Med, Jun. 4, 2001, vol. 193, No. 11, pp. 1295-1301.
Masteller, Emma, et al. "Expansion of Functional Endogenous Antigen-Specific CD4+ CD25+ Regulatory T Cells from Nonobese Diabetic Mice[1]," The Journal of Immunology, 2005, vol. 175, No. 5, pp. 3053-3059.
Tang, Q., et al. "In Vitro-expanded Antigen-specific Regulatory T Cells Suppress Autoimmune Diabetes," The Journal of Experimental Medicine, Jun. 7, 2004, vol. 199, No. 11, pp. 1455-1465.
Tang, Q., et al. "Regulatory T-cell physiology and application to treat autoimmunity," Immunological Reviews, 2006, vol. 212, pp. 217-237.
Tarbell, K., et al. "CD25+ CD4+T Cells, Expanded with Dendritic Cells Presenting a Single Autoantigenic Peptide, Suppress Autoimmune Diabetes," Jun. 7, 2004, vol. 199, No. 11, pp. 1467-1477.
Akamizu, Takashi, "Monoclonal Antibodies to Thyroid Specific Autoantigens," Autoimmunity, 2003, vol. 36, No. 6-7, pp. 361-366.
Apostolou, et al. "In Vivo Instruction of Suppressor Commitment in Naïve T Cells," J. Exp. Med., The Journal of Experimental Medicine, 2004, vol. 199, No. 10, pp. 1401-1408.
Butterfield, et al. T-Cell responses to HLA-A*0201 Immunodominant Peptides Derived from a-Fetoprotein n Patients with Hepatocellular Cancer, Clinical Cancer Research, 2003, vol. 9, No. 16, pp. 5902-5908.
Fu, et al., "CD4+ CD25+ CD62+ T-Regulatory Cell Subset Has Optimal Suppressive and Proliferative Potential," American Journal of Transplantation, 2004, vol. 4, pp. 65-78.
Green, E. Allison, et al. "CD4+CD25+T regulatory cells control anti-islet CD8+T Cells through TGF-β—TGF- β receptor interactions in type 1 diabetes," PNAS, 2003, vol. 100, No. 19, pp. 10878-10883.
Jaeckel, et al. "Antigen-Specific FoxP3-Transduced T-Cells Can Control Established Type 1 Diabetes," Diabetes, 2005, vol. 54, pp. 306-310.
Kita, Hirota, et al. "Application of tetramer technology in studies on autoimmune diseases," Autoimmunity Reviews, 2003, vol. 2, pp. 43-49.

(Continued)

Primary Examiner—Amy E Juedes
(74) Attorney, Agent, or Firm—Townsend and Townsend and Crew LLP

(57) ABSTRACT

The invention provides methods for producing an autoantigen-specific regulatory T cell enriched composition, and resultant compositions and methods of use.

9 Claims, No Drawings

OTHER PUBLICATIONS

Kukreja, Anjli, et al. "Multiple immuno-regulatory defects in type-1 diabetes," The Journal of Clinical Investigation, 2002, vol. 109, No. 1, pp. 131-140.

Mallat, Ziad, et al. Induction of a Regulatory T Cell type 1 Response Reduces the Development of Atherosclerosis in Apolipoprotein E-Knockout Mice, Circulation, 2003, vol. 108, No. 10, pp. 1232-1237.

Mekala, et al. "Immunotherapy of autoimmune encephalomyelitis with redirected CD4+ CD25+ T lymphocytes," Blood, 2005, vol. 105, No. 5, pp. 2090-2092.

Robinson, William, et al. "Protein arrays for autoantibody profiling and fine-specificity mapping," Proteomics, 2003, vol. 3, pp. 2077-2084.

Shimizu, et al. "Stimulation of $CD25^+CD4^+$ regulatory T cells through GITR breaks immunological self-tolerance," National Immunology, 2002, vol. 33, No. 2, pp. 135-142.

Suvas, et al. "$CD4^+$ $CD25^+$ Regulatory T Cells Control the Severity of Viral Immunoinflammatory Lesions[1]" Immunol 172: 4123-4132, 2004.

Thomas, et al., "A Cell-Based Artificial Antigen-Presenting Cell Coated with Anti-CD3 and CD28 Antibodies Enables Rapid Expansion and Long-Term Growth of CD4 T Lymphocytes," Clinical Immunology, 2002, vol. 105, No. 3, pp. 259-272.

Tone, et al. Mouse glucocorticoid-induced tumor necrosis factor receptor ligand is costimulatory for T-cells, PNAS, 2003, vol. 100, No. 25, pp. 15059-15064.

Yamamoto, et al. "The Activity of Immunoregulatory T Cells Mediating Active Tolerance is Potentiated in nonobese Diabetic Mice by an IL-4-Based Retroviral Gene Therapy," The Journal of Immuonology, 2001, vol. 166, pp. 4973-4980.

Yamazaki, et al. "Direct Expansion of Functional $CD25^+CD4^+$ Regulatory T Cells by Antigen-processing Dendritic Cells." 2003, J Exp Med, 198:235-247.

Yee, et al. "Isolation of High Avidity Melanoma-Reactive CTL from Heterogeneous Populations Using Peptide-MHC Tetramers," The Journal of Immunology, 1999, vol. 162, pp. 2227-2234.

Yee, et al., "Adoptive T cell therapy using antigen-specific CD8+ T Cell clones for the treatment of patients with metastatic melanoma: In vivo persistence, migration, and antitumor effect of transferred T cells," PNAS, 2002, vol. 99, No. 25, pp. 16168-16173.

* cited by examiner

SEQUENCE LISTING

<160> NUMBER OF SEQ ID NOS: 32

<210> SEQ ID NO 1
<211> LENGTH: 14
<212> TYPE: PRT
<213> ORGANISM: Homo sapiens

<400> SEQUENCE: 1

Ala Leu Asn Glu Asp Leu Ser Ser Gln Thr Ala Ala Asp Thr
1               5                   10

<210> SEQ ID NO 2
<211> LENGTH: 17
<212> TYPE: PRT
<213> ORGANISM: Homo sapiens

<400> SEQUENCE: 2

Val Val Lys Lys Gly Thr Asp Phe Gln Leu Asn Gln Leu Glu Gly Lys
1               5                   10                  15

Lys

<210> SEQ ID NO 3
<211> LENGTH: 16
<212> TYPE: PRT
<213> ORGANISM: Homo sapiens

<400> SEQUENCE: 3

Val Val Lys Lys Gly Thr Asp Phe Gln Leu Asn Gln Leu Gly Lys Lys
1               5                   10                  15

<210> SEQ ID NO 4
<211> LENGTH: 16
<212> TYPE: PRT
<213> ORGANISM: Homo sapiens

<400> SEQUENCE: 4

Tyr Val Arg Phe Asp Ser Asp Val Gly Glu Tyr Arg Ala Val Thr Glu
1               5                   10                  15

```
<210> SEQ ID NO 5
<211> LENGTH: 16
<212> TYPE: PRT
<213> ORGANISM: Homo sapiens

<400> SEQUENCE: 5

Gly Asp Gln Ser Thr Asp Tyr Gly Ile Phe Gln Ile Asn Ser Arg Tyr
1               5                   10                  15

<210> SEQ ID NO 6
<211> LENGTH: 12
<212> TYPE: PRT
<213> ORGANISM: Homo sapiens

<400> SEQUENCE: 6

Arg Gln Val Arg Phe Tyr Ser Gly Val Ile Glu Leu
1               5                   10

<210> SEQ ID NO 7
<211> LENGTH: 15
<212> TYPE: PRT
<213> ORGANISM: Homo sapiens

<400> SEQUENCE: 7

Leu Pro Asp Pro Tyr Gln Lys Gln Cys Asp Asp Phe Val Ala Glu
1               5                   10                  15

<210> SEQ ID NO 8
<211> LENGTH: 13
<212> TYPE: PRT
<213> ORGANISM: Homo sapiens

<400> SEQUENCE: 8

Ile Phe Leu Asp Asp Pro Gln Ala Val Ser Asp Val Leu
1               5                   10

<210> SEQ ID NO 9
<211> LENGTH: 12
<212> TYPE: PRT
<213> ORGANISM: Homo sapiens

<400> SEQUENCE: 9

Lys Thr Ala Phe Asp Glu Ala Ile Ala Glu Leu Asp
1               5                   10

<210> SEQ ID NO 10
<211> LENGTH: 20
<212> TYPE: PRT
<213> ORGANISM: Homo sapiens

<400> SEQUENCE: 10

Ser Thr Gln Leu Ile Arg Asn Gly Asp Trp Thr Phe Gln Val Leu Val
1               5                   10                  15

Met Leu Glu Met
            20

<210> SEQ ID NO 11
<211> LENGTH: 20
<212> TYPE: PRT
<213> ORGANISM: Homo sapiens
```

```
<400> SEQUENCE: 11

His His Asn Thr Leu Val Cys Ser Val Thr Asp Phe Tyr Pro Ala Lys
1               5                   10                  15

Ile Lys Val Arg
            20

<210> SEQ ID NO 12
<211> LENGTH: 20
<212> TYPE: PRT
<213> ORGANISM: Homo sapiens

<400> SEQUENCE: 12

Ser Met Val Thr Leu Gly Cys Leu Val Lys Gly Tyr Phe Pro Glu Pro
1               5                   10                  15

Val Thr Val Thr
            20

<210> SEQ ID NO 13
<211> LENGTH: 15
<212> TYPE: PRT
<213> ORGANISM: Homo sapiens

<400> SEQUENCE: 13

Phe Val Asn Gln His Leu Cys Gly Ser His Leu Val Glu Ala Leu
1               5                   10                  15

<210> SEQ ID NO 14
<211> LENGTH: 15
<212> TYPE: PRT
<213> ORGANISM: Homo sapiens

<400> SEQUENCE: 14

Pro Arg Leu Ile Ala Phe Thr Ser Glu His Ser His Phe Ser Leu
1               5                   10                  15

<210> SEQ ID NO 15
<211> LENGTH: 15
<212> TYPE: PRT
<213> ORGANISM: Homo sapiens

<400> SEQUENCE: 15

Asn Ile Leu Leu Gln Tyr Val Val Lys Ser Phe Asp Arg Ser Thr
1               5                   10                  15

<210> SEQ ID NO 16
<211> LENGTH: 15
<212> TYPE: PRT
<213> ORGANISM: Homo sapiens

<400> SEQUENCE: 16

Lys Tyr Lys Ile Trp Met His Val Asp Ala Ala Trp Gly Gly Gly
1               5                   10                  15

<210> SEQ ID NO 17
<211> LENGTH: 15
<212> TYPE: PRT
<213> ORGANISM: Homo sapiens

<400> SEQUENCE: 17

Lys His Lys Trp Lys Leu Asn Gly Val Glu Arg Ala Asn Ser Val
1               5                   10                  15
```

```
<210> SEQ ID NO 18
<211> LENGTH: 15
<212> TYPE: PRT
<213> ORGANISM: Homo sapiens

<400> SEQUENCE: 18

Leu Tyr Asn Ile Ile Lys Asn Arg Glu Gly Tyr Glu Met Val Phe
1               5                   10                  15

<210> SEQ ID NO 19
<211> LENGTH: 15
<212> TYPE: PRT
<213> ORGANISM: Homo sapiens

<400> SEQUENCE: 19

Pro Ser Leu Arg Val Leu Glu Asp Asn Glu Glu Arg Met Ser Arg
1               5                   10                  15

<210> SEQ ID NO 20
<211> LENGTH: 15
<212> TYPE: PRT
<213> ORGANISM: Homo sapiens

<400> SEQUENCE: 20

Ser Tyr Gln Pro Leu Gly Asp Lys Val Asn Phe Phe Arg Met Val
1               5                   10                  15

<210> SEQ ID NO 21
<211> LENGTH: 15
<212> TYPE: PRT
<213> ORGANISM: Homo sapiens

<400> SEQUENCE: 21

Phe Phe Arg Met Val Ile Ser Asn Pro Ala Ala Thr His Gln Asp
1               5                   10                  15

<210> SEQ ID NO 22
<211> LENGTH: 15
<212> TYPE: PRT
<213> ORGANISM: Homo sapiens

<400> SEQUENCE: 22

Ala Thr His Gln Asp Ile Asp Phe Leu Ile Glu Glu Ile Glu Arg
1               5                   10                  15

<210> SEQ ID NO 23
<211> LENGTH: 15
<212> TYPE: PRT
<213> ORGANISM: Homo sapiens

<400> SEQUENCE: 23

Thr Tyr Glu Ile Ala Pro Val Phe Val Leu Leu Glu Tyr Val Thr
1               5                   10                  15

<210> SEQ ID NO 24
<211> LENGTH: 16
<212> TYPE: PRT
<213> ORGANISM: Homo sapiens

<400> SEQUENCE: 24

Pro Ala Ile Phe Lys Ser Tyr Cys Glu Ile Ile Val Thr His Phe Pro
1               5                   10                  15
```

```
<210> SEQ ID NO 25
<211> LENGTH: 17
<212> TYPE: PRT
<213> ORGANISM: Homo sapiens

<400> SEQUENCE: 25

Glu Ile Ile Val Thr His Phe Pro Phe Asp Glu Gln Asn Cys Ser Met
1               5                   10                  15
Lys

<210> SEQ ID NO 26
<211> LENGTH: 18
<212> TYPE: PRT
<213> ORGANISM: Homo sapiens

<400> SEQUENCE: 26

Asp Thr Pro Tyr Leu Asp Ile Thr Tyr His Phe Val Met Gln Arg Leu
1               5                   10                  15
Pro Leu

<210> SEQ ID NO 27
<211> LENGTH: 13
<212> TYPE: PRT
<213> ORGANISM: Homo sapiens

<400> SEQUENCE: 27

Pro Thr Phe Gly Arg Ser Phe Thr Leu Ala Ser Ser Glu
1               5                   10

<210> SEQ ID NO 28
<211> LENGTH: 12
<212> TYPE: PRT
<213> ORGANISM: Homo sapiens

<400> SEQUENCE: 28

Thr Cys Phe Phe Arg Asp His Ser Tyr Gln Glu Glu
1               5                   10

<210> SEQ ID NO 29
<211> LENGTH: 9
<212> TYPE: PRT
<213> ORGANISM: Homo sapiens

<400> SEQUENCE: 29

Ser Leu Ser Arg Phe Ser Trp Gly Ala
1               5

<210> SEQ ID NO 30
<211> LENGTH: 9
<212> TYPE: PRT
<213> ORGANISM: Homo sapiens

<400> SEQUENCE: 30

Val Val His Phe Phe Lys Asn Ile Val
1               5

<210> SEQ ID NO 31
<211> LENGTH: 14
<212> TYPE: PRT
<213> ORGANISM: Homo sapiens

<400> SEQUENCE: 31

Cys Leu Ala Val Leu Trp Val Val Lys Ser Thr Pro Ala Ser
1               5                   10
```

```
<210> SEQ ID NO 32
<211> LENGTH: 14
<212> TYPE: PRT
<213> ORGANISM: Homo sapiens

<400> SEQUENCE: 32

Phe Leu Gly Glu Leu Thr Ser Ser Glu Val Ala Thr Glu Val
1               5                   10
```

US 7,722,862 B2

REGULATORY T CELLS SUPPRESS AUTOIMMUNITY

ACKNOWLEDGEMENT OF GOVERNMENT SUPPORT

This work was supported by NIH NCRR Grant R37 A146643. The U.S. government may have rights in any patent issuing on this application.

CROSS-REFERENCE TO RELATED APPLICATIONS

This application claims priority to U.S. Pat Appl Ser. No. 60/535,085, filed Jan. 8, 2004.

BACKGROUND OF THE INVENTION

Autoimmune diseases comprise many of the most devastating and intractable ailments today, where representative autoimmune diseases include diabetes mellitus, uveoretinitis and multiple sclerosis, among others.

The potential for Tregs to actively regulate autoimmunity and induce long term tolerance has great potential application as a strategy for inducing long-lived tolerance. Taking advantage of Tregs has been complicated by an inability to expand and characterize this minor T cell subset, a population of cells reduced even further in autoimmune-prone animals and patients. For instance, recent studies have suggested that it may be impossible to reverse ongoing autoimmune diabetes due to the autoreactive T cells becoming resistant to suppression during the active phase of the disease. Prior efforts to expand Tregs ex vivo have not achieved clinically sufficient expansion, nor demonstrable in vivo efficacy (e.g. Fu et al., 2004, Am J Transplant. 4, 65-78). The low number of $CD4^+$ $CD25^+$ regulatory T cells (Tregs), their anergic phenotype and diverse antigen specificity present major challenges to harnessing this potent tolerogenic population to treat autoimmunity and transplant rejection.

A number of US Patent documents relate to T cell expansion, including Horwitz (e.g. U.S. Pat. Nos. 6,803,036 and 6,797,267, and related patent publications); U.S. Pat. No. 6,534,055; US2003/124122A1; US2003/0082806A1; US2002/0058019A1; US2002/0119568A1; US2003/0119185A1; and US2002/0019048A1.

SUMMARY OF THE INVENTION

The invention provides methods for producing an autoantigen-specific regulatory T cell enriched composition, and resultant compositions and methods of use. In one embodiment, the invention provides a method of modulating an autoimmune reaction in a subject, said method comprising (a) obtaining a population of subject-compatible cells; (b) producing an autoantigen-specific regulatory T cell enriched composition from said population of cells; and (c) introducing said composition into said subject to modulate said autoimmune reaction in said subject.

In particular embodiments, the population of cells is obtained from said subject, obtained from a donor distinct from said subject, and/or harvested from peripheral blood.

In particular embodiments, the producing step comprises expanding said antigen-specific regulatory T cells, and/or enriching said autoantigen-specific regulatory T cells from said obtained population of cells.

In particular embodiments, the expanding is achieved by contacting said population of cells with an autoantigen-specific regulatory T cell stimulatory composition.

In particular embodiments, the regulatory T cells are enriched from said population of cells prior to said expanding step, or after said expanding step.

In particular embodiments, the stimulatory composition comprises an MHC class II/autoantigenic peptide complex, a costimulatory agent or a second regulatory T cell stimulatory agent.

In particular embodiments, the costimulatory agent is an agonist antibody, such as an agonist antibody which binds to CD28.

In particular embodiments, the second stimulating agent is a cytokine, such as an interleukin, such as interleukin-2.

In particular embodiments, the stimulatory composition is immobilized on a substrate, such as a cell or bead.

In particular embodiments, the producing step comprises

In particular embodiments, the said modulating comprises inhibiting.

The invention also provides compositions comprising a population of cells wherein at least 50% of said cells of said composition are natural autoantigen-specific regulatory T cells.

In particular embodiments, the autoantigen-specific regulatory T cells are specific for peptides presented in MHC class II molecules as shown in Table A.

In particular embodiments, the autoantigen-specific regulatory T cells are effective at modulating an autoimmune reaction when administered to a subject.

The invention also provides kits for producing a composition of autoantigen-specific regulatory T cells, said kit comprising: (a) an autoantigen-specific T cell receptor stimulatory agent; and (b) a costimulatory agent.

In particular embodiments, the stimulatory agent is an MHC class II/autoantigenic peptide complex.

In particular embodiments, the costimulatory agent is an agonist antibody, such as an antibody which binds to CD28.

In particular embodiments, the kit further comprises a second regulatory T cell stimulating agent, such as a cytokine, such as an interleukin, such as interleukin-2 or interleukin-15.

In particular embodiments, the stimulatory agent and said costimulatory agent are immobilized on a substrate, such as a cell or bead.

The invention provides methods and compositions for ex vivo expansion of therapeutic regulatory T cells, and resultant compositions and methods of use. The expansion methods generally comprise the steps of: isolating from a mixed population of T cells a subpopulation enriched in $CD4^+CD25^+$ T cells (Treg cells); expanding the Treg cells of the subpopulation by contacting the subpopulation with effective amounts of (i) a TCR/CD3 activator (ii) a TCR costimulator activator and (iii) IL-2, to obtain ex vivo expanded Treg cells, wherein the expanded Treg cells demonstrate immune suppression, wherein the isolating step is typically prefaced by extracting the population from a person or patient, typically suffering or in remission from an autoimmune disease amenable to therapy as described herein.

In particular embodiments, the subpopulation comprises >98% Treg cells, preferably >98% $CD4^+CD25^+CD62L^+$ Treg cells; the isolation step comprises negative and positive immuno-selection and cell sorting; the expanding step effects at least a 100-fold expansion of the subpopulation; the TCR/CD3 activator is a multivalent antibody or ligand for TCR/CD3; the TCR costimulator activator is a multivalent antibody or ligand for CD28, GITR, B7-1/2, CD5, ICOS, OX40 or CD40; the effective amount of IL-2 is 200 to 2500 IU IL-2/ml; and/or the Treg cells suppress proliferation of anti-CD3 or alloantigen stimulated $CD25^-$ T cells in vitro, or autoimmunity, including graft-versus-host disease in vivo.

In more particular embodiments:

an effective amount of the ex vivo expanded Treg cells introduced into the patient diagnosed with diabetes mellitus and presenting an indication of impaired glucose homoeostasis selected from fasting plasma glucose (FPG), post-prandial glucose (PPG), and glucose tolerance (GTT) provide a resultant improvement in the impaired glucose homoeostasis, wherein the improvement is preferably selected from an FPG of 110 mg/dL or less, a 2-hour PPG of 140 mg/dL or less, and a GTT of 140 mg/dL or less 2 hours after a 75-g glucose load;

the TCR/CD3 activator is an anti-CD3 antibody, and the TCR costimulator activator is an anti-CD28 antibody, wherein the anti-CD3 and anti-CD28 antibodies are immobilized on paramagnetic beads provided in a Treg cell:bead ratio of between 1:1 and 1:2;

the TCR/CD3 activator and the expanded Treg cells are antigen-specific, preferably wherein the TCR/CD3 activator is an MHC-peptide multimer, wherein the peptide is a diabetes-associated autoantigen peptide and the diabetes-associated autoantigen is selected from glutamic acid decarboxylase (GAD), an islet cell autoantigen (ICA) and insulin, and the TCR costimulator activator is an anti-CD28 antibody.

The invention also provides methods and compositions for adoptive cellular immunotherapy comprising the step of introducing into a patient in need thereof an effective amount of the subject ex vivo expanded Treg cells. These methods generally comprise the steps of: extracting a mixed population of T cells from a person; isolating from the population a subpopulation enriched in $CD4^+CD25^+$ T cells (Treg cells); expanding the Treg cells of the subpopulation by contacting the subpopulation with effective amounts of (i) a TCR/CD3 activator, (ii) a TCR costimulator activator, and (iii) IL-2, to obtain ex vivo expanded Treg cells; introducing into a patient an effective amount of the ex vivo expanded Treg cells; and detecting a resultant suppression of autoimmunity.

In particular embodiments, the person and patient is a patient diagnosed with diabetes mellitus and presenting an indication of impaired glucose homoeostasis selected from fasting plasma glucose (FPG), post-prandial glucose (PPG), and glucose tolerance (GTT); the subpopulation comprises >98% Treg cells; the subpopulation comprises >98% $CD4^+CD25^+CD62L^+$ Treg cells; the isolation step comprises negative and positive immuno-selection and cell sorting; the expanding step effects at least a 100-fold expansion of the subpopulation; the TCR/CD3 activator is selected from a multivalent antibody or ligand for TCR/CD3; the TCR costimulator activator is a multivalent antibody or ligand for CD28, GITR, CD5, ICOS, OX40 or CD40L; the effective amount of IL-2 is 200 to 2500 IU IL-2/ml; the Treg cells suppress proliferation of anti-CD3 or alloantigen stimulated $CD25^-$ T cells, and/or the resultant suppression of autoimmunity is detected as a resultant improvement in the impaired glucose homoeostasis.

In more particular embodiments:

the improvement is selected from an FPG of 110 mg/dL or less, a 2-hour PPG of 140 mg/dL or less, and a GTT of 140 mg/dL or less 2 hours after a 75-g glucose load;

the TCR/CD3 activator is an anti-CD3 antibody, and the TCR costimulator activator is an anti-CD28 antibody, wherein the anti-CD3 and anti-CD28 antibodies are immobilized on paramagnetic beads provided in a Treg cell:bead ratio of between 1:1 and 1:2; and/or the TCR/CD3 activator is an MHC-peptide multimer, wherein the peptide is a diabetes-associated autoantigen peptide and the diabetes-associated autoantigen is selected from glutamic acid decarboxylase (GAD), an islet cell autoantigen (ICA) and insulin, and the TCR costimulator activator is an anti-CD28 antibody.

DETAILED DESCRIPTION OF PARTICULAR EMBODIMENTS OF THE INVENTION

The invention provides methods for producing a predetermined autoantigen-specific regulatory T cell enriched composition, and resultant compositions and methods of use. In one embodiment, the invention provides a method of modulating an autoimmune reaction in a subject, said method comprising (a) obtaining a population of subject-compatible cells; (b) producing an autoantigen-specific, preferably predetermined autoantigen-specific regulatory T cell enriched composition from said population of cells; and (c) introducing said composition into said subject to modulate said autoimmune reaction in said subject.

In particular embodiments, the population of cells is obtained from said subject, obtained from a donor distinct from said subject, and/or harvested from peripheral blood. The population of cells obtained comprises autoantigen-specific regulatory T (Treg) cells, and may be derived from any source in which autoantigen-specific Treg cells exist, such as peripheral blood, the thymus, lymph nodes, spleen, and bone marrow. In certain embodiments, the source of Treg cells may be from cadaveric tissue.

The population of cells may be obtained from the subject into which the Treg-enriched composition is subsequently introduced. The subject can be any mammal in which modulation of an autoimmune reaction is desired. Mammals of interest include, but are not limited to: rodents, e.g. mice, rats; livestock, e.g. pigs, horses, cows, etc., pets, e.g. dogs, cats; and primates, e.g. humans. In one embodiment, the subject is an animal model of an autoimmune disease. There are numerous, established animal models for using T cell epitopes of autoantigens to induce tolerance, including multiple sclerosis (EAE: experimental autoimmune encephalomyelitis), myasthenia gravis (EMG: experimental myasthenia gravis) and neuritis (EAN: experimental autoimmune neuritis). In another embodiment, the subject is a human afflicted with an autoimmune disease or disorder, such as any of the diseases/disorders listed in Table A.

In an alternate embodiment, the population of cells is obtained from a donor distinct from the subject. The donor is preferably syngeneic, but can also be allogeneic, or even xenogeneic provided the cells obtained are subject-compatible in that they can be introduced into the subject, optionally in conjunction with an immunosuppressive therapy, without resulting in extensive chronic graft versus host disease (GvHD). Allogeneic donor cells are preferably human-leukocyte-antigen (HLA)-compatible, and are typically administered in conjunction with immunosuppressive therapy. To be rendered subject-compatible, xenogenic cells may be subject to gamma irradiation or PEN110 treatment (Fast, L D et al, Transfusion. February 2004; 44(2):282-5).

The producing step provides a predetermined autoantigen-specific regulatory T cell enriched composition from said population of cells, preferably specific for a predetermined autoantigen associated with the targeted autoimmune reaction, preferably predetermined to be associated with the targeted autoimmune reaction. In particular embodiments, the producing step comprises expanding said antigen-specific regulatory T cells, and/or enriching said autoantigen-specific regulatory T cells from said obtained population of cells.

An autoantigen-specific regulatory T (Treg) cell enriched composition is one in which the percentage of autoantigen-specific Treg cells is higher than the percentage of autoantigen-specific Treg cells in the originally obtained population of cells. In particular embodiments, at least 75%, 85%, 90%, 95%, or 98% of said cells of the composition are autoantigen-specific regulatory T cells. In particular embodiments, the producing step comprises expanding the antigen-specific regulatory T cells, and/or enriching said autoantigen-specific regulatory T cells from said obtained population of cells.

In particular embodiments, the regulatory T cells are enriched from said population of cells prior to said expanding step, or after said expanding step. Treg cells can be enriched by targeting for selection of cell surface markers specific for immune suppressive Tregs and separating using automated cell sorting such as fluorescence-activated cell sorting (FACS), solid-phase magnetic beads, etc, as described below in Examples 1 and 2. To enhance enrichment, positive selection may be combined with negative selection against cells comprising surface makers specific to non-Treg cell types, such as depletion of CD8, CD11b, CD16, CD19, CD36 and CD56-bearing cells, and as exemplified below.

In particular embodiments, the expanding is achieved by contacting the population of cells with an autoantigen-specific regulatory T cell stimulatory composition. The autoantigen-specific regulatory T cells are preferably expanded at least 50-fold, and preferably at least 100, 200, 300, 500 and 800-fold. Autoantigen-specific regulatory T cell stimulatory compositions promote the survival, growth, and/or expansion of autoantigen-specific regulatory T cells that express T cell receptor(s) that recognize a desired autoantigen.

Preferred stimulatory compositions stimulate the T cell by antigen-specifically binding and activating the T cell receptor complex. A variety of antigen-specific TCR-binding reagents may be used, including cross-linked peptide-bound MHC molecules, antibodies, and mimetics. In a preferred embodiment, the compositions comprises an MHC class II/autoantigenic peptide complex, particularly an aggregate of such MHC/peptide complexes. These complexes comprises at least the extracellular peptide binding domain of an MHC class II molecule in which is functionally bound an autoantigenic peptide. The complexes can be in solution or suspension or immobilized on a substrate, such as presented on the surface of a cell, particularly an APC. Numerous applicable methods are known in the art for generating functional MHC class II/peptide complexes, such as may be found in literu In one embodiment, the autoantigenic peptide is a peptide of the naturally occurring autoantigen that is capable of complexing with an MHC class II molecule. Exemplary MHC class II molecules/peptide complexes are listed in Table A. In an alternative embodiment, the autoantigenic peptide is a mimotope peptide capable of complexing with an MHC class II molecule.

In another embodiment the autoantigenic peptide is a mimotope peptide that is capable of complexing with an MHC class II molecule. Mimotope peptides are described in the literature, further below, and in Examples 1. Protocols for using autoantigen peptides to expand Tregs from otherwise conventional T cells include the use of autoantigen-specific MHC-peptide tetramers, peptide-pulsed DCs (Yamazaki, et al, 2003, J Exp Med 198:235-47) or artificial APCs (Maus et al. Nat. Biotechnol. 20:143-8, 2002) to expand Tregs from patients independent of the cell surface phenotype. In addition, a combination of in vitro and in vivo approaches can enhance the effects of the therapy. For example, recent studies have shown that administration of self antigens, altered peptide ligands and even non-specific stimuli such as FcR non-binding anti-CD3 mAbs can promote antigen-specific Treg activity (Apostolou et al. J. Exp. Med. 199:1401-8, 2003; Belghith et al. Nat. Med. 9:1202-8, 2003). Hence, combining in vivo immunization to induce the Tregs with ex vivo expansion or visa versa may be advantageous.

In certain embodiments, the stimulatory composition may further include one or more additional agents, e.g., a costimulatory agent, a second regulatory T cell stimulatory agent, or agents that generally promote the survival and/or growth of T cells.

In certain embodiments, the costimulatory agent is an antibody or ligand specific for a TCR costimulator, such as CD28 or GITR, as described below. In particular embodiments, the costimulatory agent is an agonist antibody, such as an agonist antibody which binds to CD28.

The stimulatory composition alternatively comprises a second regulatory T cell stimulatory agent. Exemplary stimulatory agents include granulocyte colony stimulating factor, interleukins such as IL-2, IL-6, IL-7, IL-13, and IL-15, and hepatocyte growth factor (HGF). In particular embodiments, the second stimulating agent is a cytokine, such as an interleukin, such as interleukin-2.

In particular embodiments, one or more components of the stimulatory composition is immobilized on a substrate, such as a cell or bead. Cells suitable for use as substrates include artificial antigen-presenting cells (AAPCs) (Kim, J V et al, Nat Biotechnol. April 2004; 22(4):403-10; and Thomas, A K et al, Clin Immunol. December 2002; 105(3):259-72). Beads can be plastic, glass, or any other suitable material, typically in the 1-20 micron range. Paramagnetic beads are preferred.

Optimal concentrations of each component of the stimulatory compositions, culture conditions and duration can be determined empirically using routine experimentation. An exemplary autoantigen-specific regulatory T cell stimulatory composition is described in Example 2.

The expanded and/or enriched autoantigen-specific regulatory T cells are introduced into the subject to modulate an autoimmune reaction. For example, the subject may be afflicted with a disease or disorder characterized by having an ongoing or recurring autoimmune reaction, such as the diseases/disorders listed in Table A. In particular embodiments, the said modulating comprises inhibiting. Tregs may serve as a "Trojan Horse" to deliver suppressive or other biologic factors to sites of inflammation, such as IL-4 (Yamamoto et al. J Immunol. 166:4973-80, 2001), stem cell growth factors, angiogenesis regulators, genetic deficiencies, etc. For example, overexpression of foxp3 has been shown to transform otherwise pathogenic T cells into Tregs (Jaeckel et al. Diabetes. Dec. 10, 2004; [Epub]), and polyclonally expanded Tregs can be transduced with genes encoding an antigen-specific TCR plus foxp3 to generate potent antigen-specific Tregs in very high numbers and efficiency (Mekala, et al., Blood. Nov. 4, 2004; [Epub]). Thus, these antigen-specific approaches decrease the requirement for high cell numbers while maximizing Treg specificity and function.

Antigen-specific Tregs are particularly indicated in infectious diseases in which the pathogenicity of the infections is not a result of the cytopathic effects of the pathogen but rather the tissue damage caused by the immunoinflammatory response to the infectious agent. In diseases, such as hepatitis C or HSV-induced corneal inflammation, Treg therapy provides a unique opportunity to control viral-induced immunoinflammatory disease (Suvas et al. J. Immunol. 172: 4123-4132, 2004). Viruses, such as Coxsackie, are known to cause pancreatitis and have been associated with the development of Type 1 Diabetes. Thus, Tregs that target expressed viral antigens can be used to suppress local tissue damage caused by the infection and reduce the inflammation that incites autoimmune disease development.

The invention also provides compositions comprising a population of cells wherein at least 50% of said cells of said composition are natural (nontransformed), preferably expanded autoantigen-specific regulatory T cells, wherein the autoantigen-specificity is preferably predetermined, preferably predetermined to a targeted autoimmune reaction antigen. The compositions are made by the methods described herein. The percentage of the autoantigen-specific regulatory T cells in the composition can be ascertained using the methodology described in Example 2. In particular embodiments, at least 75%, 85%, 90%, 95%, or 98% of said cells of the composition are autoantigen-specific regulatory T cells.

In particular embodiments, the autoantigen-specific regulatory T cells are specific for an MHC class II molecule/peptide complex listed in Table A.

In particular embodiments, the autoantigen-specific regulatory T cells are effective at modulating an autoimmune reaction when administered to a subject. Effective and optimized dosages and treatment regimes using the expanded and/or enriched autoantigen-specific regulatory cells are informed from vast clinical experience with existing T-cell infusion therapies, and can be further determined empirically.

The subject methods find use in the treatment of a variety of different conditions in which the modulation of an aberrant immune response in the host is desired. By aberrant immune response in a host is meant any immune reaction in a subject characterized as an autoimmune response (e.g., an autoimmune disease). In general, autoimmune responses occur when the immune system of a subject recognizes self-antigens as foreign, leading to the production of self-reactive effector immune cells. Self reactive effector immune cells include cells from a variety of lineages, including, but not limited to, cytotoxic T cells, helper T cells, and B cells. While the precise mechanisms differ, the presence of autoreactive effector immune cells in a host suffering from an autoimmune disease leads to the destruction of tissues and cells of the host, resulting in pathologic symptoms. Numerous assays for determining the presence of such cells in a host, and therefore the presence of an autoimmune disease, such as an antigen specific autoimmune disease in a host, are known to those of skill in the art and readily employed in the subject methods. Assays of interest include, but are not limited to, those described in: Autoimmunity. September-November 2003; 36(6-7):361-6; J Pediatr Hematol Oncol. December 2003; 25 Suppl 1:S57-61; Proteomics. November 2003; 3(11):2077-84; Autoimmun Rev. January 2003; 2(1):43-9.

By treatment is meant that at least an amelioration of the symptoms associated with the aberrant immune response in the host is achieved, where amelioration is used in a broad sense to refer to at least a reduction in the magnitude of a parameter, e.g. symptom, associated with the condition being treated. As such, treatment also includes situations where the pathological condition, or at least symptoms associated therewith, are completely inhibited, e.g. prevented from happening, or stopped, e.g. terminated, such that the host no longer suffers from the condition, or at least the symptoms that characterize the condition.

A variety of hosts are treatable according to the subject methods. In certain embodiments, such hosts are "mammals" or "mammalian," where these terms are used broadly to describe organisms which are within the class mammalia, including the orders carnivore (e.g., dogs and cats), rodentia (e.g., mice, guinea pigs, and rats), and primates (e.g., humans, chimpanzees, and monkeys). In many embodiments, the hosts will be humans.

In further embodiments, the methods include a step of diagnosing the presence of an autoimmune disease. By diagnosing is meant that the autoimmune response of a subject is generally classified, e.g., diabetes mellitus, SLE, MS, etc. Further, at least one autoantigen is identified to which the aberrant immune response is directed. A variety of diagnostic methods are known in the art and are currently being developed. As such, the methods of the subject invention are not limited to specific assays for diagnosing the autoimmune disease in a host or the antigen to which it is directed.

Also provided are reagents and kits thereof for practicing one or more of the above-described methods. The subject reagents and kits thereof may vary greatly. In certain embodiments, the kits include at least an antigen specific regulatory T cell stimulatory composition. In other embodiments, the kit includes another regulatory T cell stimulating agent, such as a cytokine, such as an interleukin, such as interleukin-2 or interleukin-15. In certain embodiments, the kits may further include reagents for performing the antigen specific regulatory T cell expansion step, including culture dishes or flasks, culture medium, or any necessary buffers, factors, etc. In yet other embodiments, the kits include the means to harvest the sample containing the regulatory T cells and the reagents necessary to perform regulatory T cell enrichment/purification.

In addition to the above components, the subject kits will further include instructions for practicing the subject methods. These instructions may be present in the subject kits in a variety of forms, one or more of which may be present in the kit. One form in which these instructions may be present is as printed information on a suitable medium or substrate, e.g., a piece or pieces of paper on which the information is printed, in the packaging of the kit, in a package insert, etc. Yet another means would be a computer readable medium, e.g., diskette, CD, etc., on which the information has been recorded. Yet another means that may be present is a website address which may be used via the internet to access the information at a removed site. Any convenient means may be present in the kits.

In particular embodiments, the stimulatory agent is an MHC class II/autoantigenic peptide complex. Exemplary MHC class II molecules/peptide complexes are listed in Table A.

The costimulatory agent is an antibody or ligand specific for a TCR costimulator, such as CD28 or GITR, as described below. In particular embodiments, the costimulatory agent is an agonist antibody, such as an antibody which binds to CD28.

In particular embodiments, the stimulatory agent and said costimulatory agent are immobilized on a substrate, such as a cell or bead.

The invention provides methods and compositions for ex vivo expansion of therapeutic regulatory T cells (Treg cells), and the use of such expanded Treg cells for adoptive cellular immunotherapy to suppress autoimmunity.

The expansion methods generally comprise first extracting a mixed population of T cells from a person or patient, and isolating from the population a subpopulation enriched in Treg cells. To maximize efficacy, the subpopulation is enriched to at least 90%, preferably at least 95%, and more preferably at least 98% Treg cells, preferably $CD4^+CD25^+CD62L^+$ Treg cells. Cells are generally enriched by targeting for selection cell surface markers specific for immune suppressive Tregs and separating using automated cell sorting such as fluorescence-activated cell sorting (FACS), solid-phase magnetic beads, etc. To enhance enrichment, positive selection may be combined with negative selection against cells comprising surface makers specific to non-Treg cell types, such as depletion of CD8, CD11b, CD16, CD19, CD36 and CD56-bearing cells, and as exemplified below.

The Treg-enriched subpopulation is then expanded ex vivo by culturing the cells in the presence of effective amounts of a TCR/CD3 activator, a TCR costimulator activator, and IL-2. The TCR/CD3 activator is selected from a multivalent antibody or ligand for TCR/CD3, including antigen non-specific activators such as an anti-CD3 antibody, and antigen-specific activators, such as an MHC-peptide multimer (see, e.g. Yee, et al., Adoptive T cell therapy using antigen-specific CD8+ T cell clones for the treatment of patients with metastatic melanoma: In vivo persistence, migration, and antitumor effect of transferred T cells. Proc Natl Acad Sci USA, Dec. 10, 2002; 99(25): 16168-16173; Butterfield, et al., T-Cell responses to HLA-A*0201 immunodominant peptides derived from a-fetoprotein in patients with hepatocellular cancer, Clin. Cancer Res., Dec. 1, 2003; 9(16): 5902-5908; and Yee, et al., Isolation of high avidity melanoma-reactive CTL from heterogeneous populations using peptide-MHC tetramers, J Immunol, 1999, 162: 2227-223), wherein the peptide is typically an autoimmune disease associated peptide, such as a diabetes-associated autoantigen peptide wherein suitable diabetes-associated autoantigens include glutamic acid decarboxylase (GAD), an islet cell autoantigen (ICA) and insulin, wherein combinations of such peptides may also be used.

The costimulator activator is a multivalent antibody or ligand specific for a TCR costimulator, preferably CD28 or GITR (Shimizu et al., Stimulation of CD25(+)CD4(+) regulatory T cells through GITR breaks immunological self-tolerance, Nat Immunol. February 2002; 3(2):135-42. Epub Jan. 22, 2002; Tone et al., Mouse glucocorticoid-induced tumor necrosis factor receptor ligand is costimulatory for T cells, Proc Natl Acad Sci USA. Dec. 9, 2003; 100(25):15059-64. Epub Nov. 7, 2003), though alternative TCR costimulators such as CD5, ICOS, OX40 and CD40L may also be targeted where suitable expansion is so obtained, as may be determined empirically. To promote activation and expansion, the TCR/CD3 and TCR costimulator activators are typically immobilized on a 3-dimensional solid surface, such as a host cell (e.g. Thomas et al, December 2002, Clin Immunol 105, 259-72) or bead. In a particular embodiment, the activators are immobilized on paramagnetic beads provided in a Treg cell:bead ratio of between 2:1 and 1:5, preferably between 1:1 and 1:3. Optimal bead size is empirically determined, though typically in the range of 1 to 20 micron diameters.

The IL-2 is typically presented in recombinant form, wherein effective amounts of IL-2 are typically 200 to 2500 IU IL-2/ml. We have found increased expansions using unconventionally elevated IL-2 concentrations ranging from 500-2500, and preferably 1000-2000 IU IL-2/ml. The target Treg cells of the subpopulation are preferably expanded at least 50-fold, and preferably at least 100, 200 or 300-fold. Maximal expansions are determined empirically and will vary by cell type, incubation conditions, etc. For exemplified embodiments, maximal expansions are found to be about 300, 500 and 800-fold.

The suppressive function of the expanded Treg cells may be detected in vitro or in vivo. For example, in vitro, the expanded Treg cells may be shown to suppress proliferation of $CD25^-$ T cells stimulated with anti-CD3 in the presence of Fc-receptor-bearing cells, or $CD25^-$ T cells stimulated with irradiated allogeneic splenocytes. Suitable exemplary in vivo animal model and human clinical immune suppression protocols are described further below.

In particular embodiments, the TCR/CD3 activator and the expanded Treg cells are autoantigen-specific. For example, in a particular such embodiment, an effective amount of the ex vivo expanded Treg cells introduced into the patient diagnosed with diabetes mellitus (see, e.g. Mayfield et al., Diagnosis and classification of diabetes mellitus: new criteria, Am Fam Physician. Oct. 15, 1998; 58(6):1355-62, 1369-70) and presenting an indication of impaired glucose homoeostasis, such as fasting plasma glucose (FPG), post-prandial glucose (PPG), and glucose tolerance (GTT) provide a resultant improvement in the impaired glucose homoeostasis, particularly wherein the improvement is selected from an FPG of 110 mg/dL or less, a 2-hour PPG of 140 mg/dL or less, and a GTT of 140 mg/dL or less 2 hours after a 75-g glucose load. Accordingly, the invention provides methods and compositions for adoptive cellular immunotherapy comprising introducing into a patient in need thereof an effective amount of the subject ex vivo expanded Treg cells.

These applications generally involve reintroducing expanded Treg cells extracted from the same patient, though the methods are also applicable to adoptive cellular immunotherapy for treatment of graft-versus-host disease associated with transplantation, particularly bone marrow transplantation using Tregs derived from donor tissue.

Adoptive transfer of Tregs expanded as disclosed herein is effective to suppress a wide variety of pathogenic autoimmune responses, including diabetes, GVHD, Lupus, rheumatoid arthritis, psoriasis, multiple sclerosis, degenerative heart disease (e.g. Ziad Mallat, et al. Induction of a Regulatory T Cell Type 1 Response Reduces the Development of Atherosclerosis in Apolipoprotein EBKnockout Mice, Circulation. Sep. 9, 2003; 108(10):1232-7), inflammatory bowel disease (Crohn's disease), etc., as demonstrated in documented animal models and human clinical trials, as exemplified below.

In our adoptive cell transfer protocols, a mixed population of T cells is initially extracted from a target donor. Depending on the application, the T cells may be extracted during a period of remission, or during active disease. Typically this is done by withdrawing whole blood and harvesting granulocytes by leukapheresis (leukopheresis). For example, large volume leukapherisis (LVL) has been shown to maximize blood leukocyte yield. Harvests reach $20 \times 10^6$ cells/L using a continuous flow apheresis device (Spectra, COBE BCT). Symptoms of hypocalcemia are avoided by a continuous infusion of calcium administrated throughout leukapheresis. Typically 15-45 liters of fluid corresponding to about 4 total blood volumes are harvested during a period of time ranging from about 100 to 300 minutes.

The harvested lymphocytes may be separated by flow cytometry or other cell separation techniques based on Treg-specific cell markers such as CD4, CD25 and CD62, expanded as described herein, and then transfused to a patient, typically the cell donor (except in GVHD where the donor and recipient are different), for adoptive immune suppression. Alternatively, the cells may be frozen for storage and/or transport prior to and/or subsequent to expansion. For antigen non-specific expansions, approximately $10^9$ to $10^{11}$ Tregs are transfused; for antigen-specific expansions, therapeutically effective transfusions typically require about $10^7$ to $10^9$ Treg cells.

Graft Versus Host Disease (GVHD). Ex vivo expanded $CD4^+$ $CD25^+$ cells inhibit GVHD generation in our experimental protocol adapted from Taylor, et al. Blood 99, 3493-9 (2002). $2 \times 10^6$ freshly purified B6 $CD4^+$ T cells plus $5 \times 10^6$ bone marrow cells are infused into irradiated, BALB/c×B6 (F1) recipients. Cohorts of mice receive a separate injection of $2 \times 10^6$ activated $CD4^+CD25^+$ cells or $CD4^+CD25^-$ cells, and survival and weights are monitored. The infusion of ex vivo-expanded $CD4^+CD25^+$ cells significantly increases the median survival time from 10 days to greater than 100 days in 80% of mice. Survival in mice receiving supplemental expanded CD4+CD25− cells is not significantly different from control mice receiving only fresh CD4+ T cells, indicating that the protective effect is specific to the expanded CD4+ CD25+ population. Similar results are obtained using fresh (nonexpanded) donor-derived CD4+CD25+ Treg cells to prevent GVHD lethality in an experimental protocol adapted from Edinger, et al. Nat Med 9, 1144-50 (2003). Animals that receive ex vivo expanded Treg cells at a 1:1 ratio with conventional cells are protected from acute lethal GVHD, and >80% survive more than 100 days.

Graft-versus-tumor (GVT) activity of Tconv cells is also maintained after cotransplantation of expanded Treg cells. GVHD is evaluated by clinical features and survival, tumor growth and rejection. A20-luc/yfp cells injected at the time of BMT migrate to the bone marrow, resulting in leukemia with secondary infiltration of liver and lymphoid organs (Edinger, et al. Blood 101, 640-648 (2003). BALB/c mice transplanted with TCD BM from C57BL/6 animals and coinjected with $1 \times 10^4$ A20-luc/yfp leukemia cells die before day 36 from leukemia, as demonstrated by an increase in bioluminescence imaging (BLI) signal intensity over time. BLI images show that tumor cells infiltrate the bone marrow of humerus, femur and sternum 5 d after transplantation and additional organs, including the spleen, before day 15. Animals that receive TCD BM and Tconv cells die even earlier from GVHD, but show initial engraftment of the A20-luc/yfp leukemia with a tumor cell distribution similar to that of the bone marrow only control group. In contrast, the majority of animals receiving Tconv cells with CD4+CD25+ Treg cells survive the observation period of 60 d. None of the animals show growth of leukemia, although all showed an initial tumor signal from the bone marrow at day 5, demonstrating that T-cell transplantation does not interfere with the engraftment of A20-luc/ yfp cells, but that an active eradication of leukemia cells is achieved when animals are protected from lethal GVHD by donor CD4+CD25+ Treg cells. These data demonstrate that GVHD suppression by our expanded CD4+CD25+ Treg cells does not abrogate GVT activity of adoptively transferred donor Tconv cells.

Multiple Sclerosis (MS). Numerous studies have suggested that loss of Treg cell is responsible for the lack of immunoregulation observed in patients with MS (e.g. Putheti et al., Eur J Neurol. September 2003; 10(5):529-35; Baecher-Allan et al., J Immunol, 167:1245-53. 2001; Baecher-Allan et al, J Immunol. 2002. 169(11):6210-7; Schmied, et al., Clin Immunol. March 2003; 106(3):163-74), and that adoptive cell therapy may ameliorate disease (e.g. Muraro et al. Immunological questions on hematopoietic stem cell transplantation for multiple sclerosis, Bone Marrow Transplant. August 2003; 32 Suppl 1:S41-4; Blevins et al. Future immunotherapies in multiple sclerosis, Semin Neurol. June 2003; 23(2): 147-58; Kohm, et al., Cutting Edge: CD4+CD25+ Regulatory T Cells Suppress Antigen-Specific Autoreactive Immune Responses and Central Nervous System Inflammation During Active Experimental Autoimmune Encephalomyelitis, J. Immunol., Nov. 1, 2002; 169(9): 4712-4716. Eur J Neurol. September 2003; 10(5):529-35).

In our initial studies of adoptive immunosuppression therapy with MS patients, T cells are harvested at time of remission, and Tregs are expanded with anti-CD3 and anti-CD28 antibodies (supra), and freeze-stored. The expanded Tregs are infused by injection at time of relapse, and disease progression is monitored using gadolinium-enhanced lesions (e.g. Horsfield et al., Guidelines for using quantitative magnetization transfer magnetic resonance imaging for monitoring treatment of multiple sclerosis, J Magn Reson Imaging. April 2003; 17(4):389-97). In subsequent studies, antigen-specific expansion is effected using DR2 MHC coupled with immunogenic peptides of myelin basic protein (MBP), myelin oligodendroctye glycoprotein (MOG), proteolipid protein (PLP). Separation, expansion and freeze storage is carried out as above, except that expansion is effected with MHC peptide multimers (supra) plus anti-CD28 antibody and IL-2.

Rheumatoid Arthritis (RA). Prior studies have suggested that loss of Treg cell is responsible for the lack of immunoregulation observed in patients with RA, and animal models for therapeutic intervention have been validated. For example, a particular animal model of chronic inflammatory arthritis, ovalbumin-induced arthritis (OIA) has been used to specifically analyze the role of defined populations of antigen-specific T cells; see, Hardung, Regulatory function of antigen-specific T helper cell subsets in a murine arthritis model, Proc 34th Ann Meet German Soc Immunol, Berlin, Sep. 24-27, 2003. In this system, transfer of activated antigen-specific T helper cells (Ova-TCR$^{tg/tg}$) into naive, congenic recipients was sufficient to induce joint inflammation after intraarticular injection of the antigen. Transfer of Th1 cells polarized in vitro resulted in an acute and chronic joint inflammation. Furthermore co-transfer of Ova-TCR$^{tg/tg}$ CD4+CD25+ regulatory T cells prevented the induction of the disease.

In our initial studies of adoptive immunosuppression therapy with RA patients, T cells are harvested at time of remission from PBMC or from joint synovial fluid (Cao et al. Isolation and functional characterization of regulatory CD25$^{bright}$CD4+ T cells from peripheral blood or the target organ of patients with rheumatoid arthritis. Eur J Immunol. January 2003; 33(1):215-23) and Tregs are expanded with anti-CD3 and anti-CD28 antibodies (supra) and IL-2, and freeze-stored. The expanded Tregs are infused by injection at time of relapse, and disease progression is monitored using established clinical criteria (Felson et al, The American College of Rheumatology preliminary core set of disease activity measures for rheumatoid arthritis clinical trials. The Committee on Outcome Measures in Rheumatoid Arthritis Clinical Trials. Arthritis Rheum June 1993; 36(6):729-40; Felson et al., American College of Rheumatology. Preliminary definition of improvement in rheumatoid arthritis, Arthritis Rheum June 1995; 38(6):727-35).

In subsequent studies, antigen-specific expansion is effected using DR4 MHC coupled with peptides for RA-associated autoantigens such as heat-shock proteins (HSPs), MHC-derived peptides, and joint-specific antigens such as type II collagen (e.g. Kotzin, Use of soluble peptide-DR4 tetramers to detect synovial T cells specific for cartilage antigens in patients with rheumatoid arthritis, Proc Natl Acad Sci USA Jan. 4, 2000; 97(1):291-6). Separation, expansion and freeze storage is carried out as above, except that expansion is effected with MHC peptide multimers (supra) plus anti-CD28 antibody and IL-2.

Psoriasis. Prior studies have suggested that loss of Treg cell is responsible for the lack of immunoregulation observed in patients with psoriasis, and animal models for therapeutic intervention has been validated (see, e.g. Elder et al., Of genes and antigens: the inheritance of psoriasis. J Invest Dermatol. November 1994; 103, 5 Suppl, 150S-153S).

In our initial studies of adoptive immunosuppression therapy with psoriasis patients, T cells are harvested at time of remission from PBMC, or during active disease from skin and Tregs are expanded with anti-CD3 and anti-CD28 (supra) antibodies and IL-2, and freeze-stored. The expanded Tregs are infused by injection at time of relapse, and disease progression is monitored using established clinical criteria wherein the primary clinical end point is the mean percentage change in the PASI score comparing baseline and week 12 scores (see, e.g. Ashcroft et al., Clinical measures of disease severity and outcome in psoriasis: a critical appraisal of their quality. Br J Dermatol. August 1999; 141(2):185-91)

In subsequent studies, antigen-specific expansion is effected using DR6 MHC coupled with peptides of psoriasis-associated skin autoantigens, and in the case of psoriatic arthritis, joint autoantigens. Separation, expansion and freeze storage is carried out as above, except that expansion is effected with MHC peptide multimers (supra) plus anti-CD28 antibody and IL-2.

Inflammatory Bowel Disease (IBD), Crohn's Disease, colitis. Prior studies have suggested that loss of Treg cell is responsible for the lack of immunoregulation observed in patients with IBD, and animal models for therapeutic intervention has been validated (see, e.g. Assessman et al., Colitogenic Th1 cells are present in the antigen-experienced T cell pool in normal mice: control by CD4+ regulatory T cells and IL-10. J Immunol. Jul. 15, 2003; 171(2):971-8; Read, et al., 1998. $CD38^+CD45RB^{low}CD4^+$ T cells: A T cell population with immune regulatory activities in vitro. Eur. J. Immunol. 28:3435; Mason et al, 1998. Control of Immune Pathology by regulatory T cells. Curr. Opin. in Immunol. 10:649; Asseman, et al., 1999. IL-10 is required for the generation of a population of T cells, which regulate inflammatory responses in the intestine. J. Exp. Med. 190:995).

In our initial studies of adoptive immunosuppression therapy with IBD patients, T cells are harvested at time of remission from PBMC, or during active disease from affected intestinal tissue, and Tregs are expanded with anti-CD3 and anti-CD28 antibodies (supra) and IL-2, and freeze-stored. The expanded Tregs are infused by injection at time of relapse, and disease progression is monitored using established clinical criteria correlated with histologic evidence of gastroenteritis including moderate to severe infiltrates of inflammatory cells, chronic intermittent, long duration diarrhea, weight loss, vomiting, etc., wherein alternative sources of intestinal inflammation have been clinically excluded.

In subsequent studies, antigen-specific expansion is effected using HLA-CW6 coupled with peptides of dietary and/or bacterial antigens associated with IBD hypersensitivity. Separation, expansion and freeze storage is carried out as above, except that expansion is effected with MHC peptide multimers (supra) plus anti-CD28 antibody and IL-2.

The invention provides Treg cell compositions made by the subject methods, particularly compositions adapted for transfusion into patients in need of autoimmune suppression, as described herein. For example, such compositions include effective transfusable unit dosages of expanded Treg cells as described herein, wherein such dosages may be prepackaged with in kits as described below.

The invention provides kits comprising reagent(s) and/or material(s) for use in a subject method, and optionally, an instructional medium describing a subject method. The invention also provides business methods specifically adapted to, and/or incorporating a description of, or reference to a subject method or kit.

ADDITIONAL EXAMPLES

Example 1

In Vitro Expanded Antigen-Specific Treg Cells Suppress Autoimmune Diabetes

Here we describe a robust method to expand antigen-specific Tregs from autoimmune-prone non-obese diabetic (NOD) mice. The Tregs, expanded up to 200-fold in less than 2 weeks in vitro, express a classical Treg phenotype, retaining all the quintessential characteristics of this subset including expression of CD25, CD62L, FoxP3, and GITR, and function both in vitro and in vivo to suppress effector T cell functions. The ability of expanded NOD Tregs to suppress diabetes in prediabetic and diabetic mice in vivo was significantly enhanced using the autoantigen-specific T cells when compared to polyclonal Tregs. Antigen-specific Tregs effectively suppressed the development of diabetes in Treg-deficient $CD28^{-/-}$ mice, blocked syngeneic islet graft rejection in chronically diabetic animals and, in contrast to previous reports, Tregs are shown, for the first time, to reverse diabetes in mice with new onset disease. Hence, this is the first demonstration that small numbers of antigen-specific Tregs can reverse diabetes following disease onset, providing a novel approach to cellular immunotherapy for autoimmunity.

Expansion of Regulatory T cells from autoantigen-specific TCR transgenic NOD mice. Previous studies have shown that Tregs decrease in number and function in NOD mice over time correlating with clinical disease by 16-24 weeks of age. However, the ability to use these cells therapeutically is contraindicated by the small numbers of cells resident in the circulation or lymphoid organs (<5% of $CD4^+$ T cells in NOD mice and <2% of $CD4^+$ T cells in humans with T1D). Moreover, a large number of cells are required due to difficulty selecting the cells based on antigen specificity. Therefore, we developed a technique for rapid and efficient expansion of autoantigen-specific Tregs based on observations that these cells, present in TCR transgenic (Tg) mice, can be driven into cell cycle with co-immobilized anti-CD3 and anti-CD28 antibodies plus exogenous IL-2. FACS-purified NOD Tregs cultured with anti-CD3/anti-CD28-coated beads in the presence of IL-2 expanded 150-225 fold in 11 days. In general, the $CD4^+CD25^-$ T cells expanded more vigorously (ranging from 300-800-fold in multiple experiments). Thus, a purity of >98% $CD4^+CD25^+CD62^+$T cells was preferred for successful Treg expansion as a small contamination of either $CD25^-$ $CD4^+$ or $CD8^+$ T cells impacted the ability to expand the Tregs.

Previous studies have reported that $CD4^+CD25^+$ Tregs, isolated from young NOD mice suppressed the ability of Teff cells from diabetic NOD mice to transfer disease in immunodeficient NOD mice. However, the process was inefficient and the suppressive effects of Tregs in this setting required a 0.5:1 or 1:1 ratio of Treg:Teff, likely due to the low precursor frequency of antigen-specific Tregs. Thus, we examined whether Tregs from two different antigen-specific TCR Tg mice could be expanded in vitro using the same methodology as with the polyclonal NOD Tregs. BDC2.5 TCR Tg mice express a TCR specific for an islet antigen expressed in the granules of β cells while the GAD286 TCR Tg recognizes a peptide derived from the islet antigen, glutamic acid decarboxylase (GAD). Tregs were purified from BDC2.5 and GAD286 mice and expanded using the anti-CD3/anti-CD28 plus IL-2 cocktail. The BDC2.5 cells expressed the transgenic TCRαβ based on efficient staining with a MHC-peptide tetramer previously shown to react with this TCR and the expanded GAD286 Tregs expressed the Tg TCRβ chain. The $CD4^+CD62L^+CD25^-$ and Tregs from BDC2.5 TCR Tg mice can be expanded at similar efficiency using immobilized MHC-peptide dimers. These results indicate that a population of $CD4^+CD25^+CD62L^+$ exist in both wild type and TCR Tg mice that can be expanded using this protocol.

We next examined the phenotype of the expanded Tregs by flow cytometry, western blot and real time PCR. The expanded Tregs maintained high levels of expression of CD25 as compared to expanded $CD25^-$ T cells, whereas the expression of CD62L remained high in both cell types. In addition, quantitative PCR showed that all the Tregs expressed high levels of SOCS2, PD-1, and CTLA-4 as compared to similarly expanded CD25⁻ T cells. Moreover, the recently identified markers neuropilin and TRAIL were also highly expressed on the expanded Tregs. A high level of cell surface GITR expression was observed on the expanded Tregs, however, this previously identified Treg marker was also induced on the expanded CD25⁻ T cells. It should be noted that the quantitative PCR studies were performed on five separate expanded Treg populations (including both polyclonal and BDC2.5 TCR Tg Tregs) and the relative expression was highly reproducible. Finally, we examined the recently identified lineage marker for Tregs, FoxP3. As noted by both RT-PCR and western blot analyses, the expanded Tregs expressed levels of FoxP3 similar to that observed in fresh Tregs and significantly higher than fresh or expanded CD25-T cells. The RNA expression (10-fold) and protein amounts (20-fold) were consistent with previous studies of fresh Tregs although there was clearly some increase in FoxP3 in CD25⁻ Teff cells indicating that the culture conditions may induce some regulatory T cells within the CD25⁻ subset.

We also examined the ability of the expanded Tregs to secrete cytokines. Unlike activated CD25⁻ T cells, the Tregs did not produce IL-2 or IFNγ but rather expressed the immunosuppressive cytokines IL-10 and TGFβ. Thus, the extensive activation and proliferation of the Tregs does not alter the phenotype of the Tregs which remained distinct from the CD25⁻ T cell subset.

Functional activity of in vitro expanded Tregs. Previous studies have shown that Tregs can effectively suppress proliferative responses of CD25⁻ T cells stimulated with anti-CD3 and splenic APC. The expanded NOD Tregs efficiently suppressed proliferative responses and cytokine production including IL-2 and IFNγ. In fact, in multiple experiments, the expanded Tregs suppressed significantly better than fresh NOD Tregs. The suppression was routinely observed at Treg:Teff ratios of <1:10. Similar results were observed using the expanded Tregs from the TCR Tg mice as the expanded BDC2.5 Tregs were effective in suppressing the proliferative response of BDC2.5 as well as polyclonal NOD T cells. Examination of the mechanism of Treg suppression confirmed other studies demonstrating a requirement for cell-cell contact. Although the expanded Tregs expressed significant levels of IL-10 and TGFβ, suppressor activity was unaffected by the addition of anti-IL-10, anti-TGFβ or a combination of both antibodies to the in vitro cultures. These results are consistent with numerous models of Treg suppression where cell-cell contact is the primary means of immunosuppression in the in vitro setting.

To further assess the antigen-specificity of the expanded Tregs and determine whether the expanded Tregs were constitutively suppressive, expanded Tregs from normal BALB/c mice were examined for their ability to suppress T cells from the OVA-specific DO11.10 TCR Tg mouse. Tregs and DO11.10 Tg Teff cells were co-cultured in the presence of OVA antigen (to activate only the Teff cells) or anti-CD3 (to activate both the Teff and Tregs). Expanded BALB/c Tregs did not inhibit the proliferative response of the DO11.10 T cells stimulated by the OVA peptide. However, the anti-CD3 response was fully inhibited at low Treg:Teff ratios supporting the lack of constitutive suppressive activity of the expanded Tregs and the requirement for antigen-specific activation of Tregs for effective immune suppression. This result also ruled out the trivial possibility that the cells were inhibiting the cultures by consuming available IL-2 through the high level of CD25 expression.

In vivo survival and activation of expanded Tregs. Effective suppression of immune responses in vivo by Tregs requires that the cells migrate to appropriate sites, respond to antigen and survive long term. We have observed recently that blockade of the CD28/B7 pathway resulted in rapid loss of Tregs in vivo and subsequent loss of critical immune regulation. Thus, we examined the ability of expanded Tregs to survive and proliferate in vivo. Expanded Tregs from NOD, BDC2.5 and GAD286 mice were labeled with CSFE and transferred into normal non-lymphopenic NOD mice. At 7 days post transfer, the mice were sacrificed and examined for the number of CSFE⁺ cells as a read out of survival and proliferation. A significant number of CSFE⁺ cells were recovered from mice transferred with expanded Tregs from the different mouse strains. In fact, CFSE⁺ Tregs as well as Thy1.1-marked Tregs were observed at least 50 days post transfer, and the numbers were equal to those observed with fresh Tregs transferred in the same manner.

Next, we analyzed the ability of the adoptively transferred Tregs to respond to antigen and to proliferate in vivo. To obviate the potential for lymphopenia-driven proliferation, the Tregs were transferred into normal mice. A small, but significant number of Tregs, proliferated based on CSFE dilution. However, there was no selective proliferation of the NOD Tregs in the pancreatic lymph nodes (pancLN) indicating that there was not a significant number of islet autoantigen-specific cells within the NOD Treg repertoire. In fact, there were fewer expanded Tregs in the NOD pancLN cells than observed in other LN cells, indicating the possibility that islet-specific Tregs were deleted in the NOD. In contrast to the NOD Tregs, Tregs from BDC2.5 Tg mice proliferated and expanded extensively and selectively in the pancLN dividing at least 3-4 times during the 7 day period. Interestingly, the proliferating Tregs down-regulated CD62L expression. This is surprising since the cells had undergone multiple proliferative cycles in vitro prior to transfer and had maintained high levels of CD62L expression. In contrast to the BDC2.5 Tregs, the GAD286 Tregs did not proliferate in vivo. Previous studies suggest that these two TCR Tg mice differ significantly in their thymic development. The BDC2.5 Tg mice do not negatively select the islet specificity in the thymus but rather develop a small but reproducible number of Tregs that have been shown to block disease by potential effector cells resident in these animals. By comparison, GAD286 TCR Tg T cells are negatively selected in the thymus such that the cells that escape utilize alternative TCRα chains. Although the peripheral GAD286 TCR Tg cells respond to GAD peptide in vitro, the reactivity is weak and, in contrast to the BDC2.5, are unable to induce diabetes upon adoptive transfer indicating the "absence" of an autoreactive repertoire. Thus, these results using the expanded Tregs indicate that the BCD2.5 TCR Tg, but not GAD286 TCR Tg mice have circulating autoreactive Tregs that home and survive in vivo and receive additional signals to further activate and expand the antigen-specific subset.

In vitro expanded Tregs suppress adoptive transfer of diabetes in vivo. Next, we examined the ability of the expanded BDC2.5 Tregs to suppress diabetes following in vivo co-transfer of activated BDC2.5 T cells into NOD RAG mice. The Tregs were effective in blocking the transfer of diabetes, functioning at as low as a 1:9 ratio of Treg:Teff, whereas the GAD286 Tregs did not protect even at Treg:Teff of 1:1. In fact, the expanded BDC2.5 Tregs suppressed polyclonal T cell-mediated disease. As few as $2 \times 10^6$ expanded BDC2.5 Tregs blocked the ability of $25 \times 10^6$ diabetogenic NOD spleen cells to transfer disease. The expanded antigen-specific Tregs from the BDC2.5 mice were far more efficient than expanded polyclonal NOD Tregs in preventing the onset of diabetes, consistent with the distinct proliferative differences described above. As many as $8 \times 10^6$ expanded NOD Tregs prevented diabetes in only 25% of diabetogenic cell transferred RAG recipients as compared to total blockade of disease transfer using one quarter the number of the antigen-specific BDC2.5 Tregs. This result is consistent with previous findings suggesting that a high ratio of polyclonal Treg to Teff cells are necessary to efficiently suppress disease transfer in this setting. Importantly, these data indicate that in vitro reactivity of the Tregs does not predict in vivo function in this disease.

Expanded Tregs prevent diabetes in vivo in a non-lymphopenic setting. Although there are multiple models demonstrating the immunoregulatory activity of Tregs, many of the systems are based on adoptive transfer models that take advantage of lymphopenic mice to enhance Treg proliferation.[8,21-24] Therefore, we examined the ability of the expanded Tregs to prevent diabetes in a non-lymphopenic animal model. Previous studies have shown that $CD28^{-/-}$ NOD mice have normal numbers of T cells and Th1 responses. In fact, these mice develop exacerbated autoimmunity due to a deficiency in Th2 and Tregs which were shown to be exquisitely CD28-dependent. Thus, we examined whether wild type expanded BDC2.5 Tregs could be transferred into $CD28^{-/-}$ NOD mice and delay or prevent onset of disease. Five$\times 10^5$ Tregs were transferred into 5 week old $CD28^{-/-}$ NOD mice and monitored for diabetes. The transfer of expanded BDC2.5 Tregs prevented the development of diabetes in 100% of mice examined as long as 20 weeks after transfer. In contrast, the transfer of expanded NOD Tregs had no effect on disease incidence. These results indicate that the antigen-specific expanded Tregs functioned in vivo in the face of a fully functional pathogenic T cell response.

Expanded Tregs reverse diabetes in vivo. The ultimate utility of Treg therapy depends on being able to treat individuals with ongoing disease. Thus, we extended an examination of the regulatory effects of these expanded Tregs in frank models of diabetes. First, we examined the ability of expanded BDC2.5 Tregs to block rejection of a syngeneic NOD islet transplant. Normoglycemia was maintained in diabetic NOD mice using insulin pellets for at least two weeks. At that time, the mice were transplanted with 500 syngeneic islet cells alone or in conjunction with expanded Tregs. The co-transfer of $2 \times 10^6$ BDC2.5, but not $5 \times 10^6$ NOD, expanded Tregs blocked rejection of the syngeneic islets consistent with an ability of the suppressor cells to block ongoing autoimmunity in this setting. More significantly, the adoptive transfer of expanded BDC2.5 Tregs reversed diabetes in overtly diabetic NOD mice. In this setting, $1 \times 10^7$ Tregs were transferred into NOD mice diagnosed with recent disease onset based on elevated blood glucose levels (>300 mg/dL). The transferred Tregs reversed diabetes in 60% of the mice. Thus, the expanded Tregs were extremely effective in blocking and reversing diabetes in an ongoing autoimmune setting.

Our observation that the Tregs are able to reverse diabetes demonstrates the applicability of our methods for clinical autoimmune therapy, where Tregs are isolated from patients either during remission (e.g for SLE or MS) or soon after disease onset (e.g. for T1D). The cells are then expanded and reintroduced at the time of maximal disease activity to moderate the inflammatory response. We have found that this therapy can be combined with Rapamycin, Anti-CD3 or other drugs that cause deletion of the pathogenic cells without affecting the Tregs. Together these therapies both reduce the short term pathogenic responses while reinstating a homeostatic balance for long-term tolerance induction.

Example 2

Expansion of Functional Endogenous Antigen-Specific $CD4^+CD25^+$ Regulatory T Cells from NOD Mice: Antigen-Specific $CD4^+CD25^+$ Regulatory T Cells Control Autoimmune Diabetes $CD4^+CD25^+Foxp3^+$ regulatory T cells (Treg) are critical for controlling autoimmunity. Evidence suggests Treg development and function are dependent on antigen specificity. Despite this, little is known about antigen-specific Tregs arising in natural settings. In this example we identify and characterize Tregs that recognize an islet peptide-mimic and arise naturally in nonobese diabetic mice. Antigen-specific Tregs express prototypic surface markers and cytokines. Although activated in an antigen-specific fashion, the expanded Tregs were capable of bystander suppression both in vitro and in vivo. Importantly, the islet peptide mimic-specific Tregs were more efficient than polyclonal Tregs in suppressing autoimmune diabetes. Our disclosure demonstrates the utility of Tregs as therapeutics for organ-specific autoimmunity.

Autoimmune type 1 diabetes (T1D) develops due to a breakdown in the mechanisms responsible for maintaining tolerance to self-antigens, resulting in T cell-mediated destruction of the insulin-producing islet cells of the pancreas. Potentially pathogenic self-reactive T cells are present in the normal peripheral T cell repertoire but in healthy individuals are controlled in part by suppressor or regulatory T cells (Tregs) (1, 2). Among the classes of Tregs, $CD4^+CD25^+$ Tregs are a unique cell subset important for controlling autoimmunity (3, 4). Mice and humans deficient in $CD4^+CD25^+$ Tregs or Foxp3, the transcription factor that controls $CD4^+CD25^+$ Treg development and suppressor function, suffer from multiorgan autoimmune disease (5-11). A decreased or impaired suppressor function of $CD4^+CD25^+$ Tregs has been associated with T1D, multiple sclerosis, rheumatoid arthritis, and other autoimmune diseases (12-16). By comparison, the transfer of polyclonal $CD4^+CD25^+$ regulatory T cells prevented autoimmunity in a number of systems including autoimmune diabetes in nonobese diabetic (NOD) mice, a mouse model of T1D (17, 18). However, the process was inefficient and required the transfer of high numbers of Tregs. We recently described a method for the in vitro expansion of islet antigen-specific $CD4^+CD25^+$ BDC2.5 T cell receptor transgenic ($TCR Tg^+$) Tregs using a combination of IL-2 and beads coated with anti-CD3 and anti-CD28 mAb (19). The expanded islet-specific Tregs were effective in blocking and reversing diabetes in NOD mice using significantly reduced numbers of Tregs as compared to polyclonal NOD Tregs; indicating that antigen-specificity of the Tregs is important for therapeutic efficacy. Therefore, effective clinical therapy depends on the ability to identify and expand relevant antigen-specific Tregs from polyclonal populations (20).

Relatively little is known about the antigen-specificity of $CD4^+CD25^+$ Tregs arising under natural conditions. In the present study, we hypothesized that since BDC2.5 $TCR Tg^+$ mice have a significant percentage of islet antigen-specific Treg this specificity might be present in conventional NOD mice as well (19, 21, 22). Thus, we adapted the expansion protocol used in the BDC2.5 Treg studies by substituting the anti-CD3 mAb with a recombinant MHC class II $I-A^{g7}$ presenting the BDC2.5 TCR mimotope peptide 1040-31 (p31) (23). The mimotope peptide was used because the endogenous BDC2.5 antigen is not yet identified (24). To determine if p31-I-A$^{g7}$ beads could expand low frequency antigen-specific cells from a polyclonal population BDC2.5 TCR Tg$^+$ Tregs were seeded into polyclonal CD4$^+$CD25$^+$ Treg cells from NOD mice. The p31-I-A$^{g7}$ and anti-CD28 coated beads were extremely efficient in expanding CD4$^+$CD25$^+$ BDC2.5 TCR Tg$^+$ Tregs in the presence of exogenous IL-2. Cultures initially seeded at 0.1% BDC2.5 TCR Tg$^+$ Tregs expanded approximately 4-fold, whereas cultures seeded at 0.01% and 0.001% BDC2.5 TCR Tg$^+$ Tregs did not expand appreciably. However, flow cytometry analysis using p31-I-A$^{g7}$ multimers to detect antigen-specific cells revealed that BDC2.5 TCR Tg$^+$ Tregs had expanded in all cultures. At the lowest seeding, BDC2.5 TCR Tg$^+$ Tregs grew from 0.001% to 34.3% of the population. This reflected greater than 12 cell divisions during the culture period resulting in nearly a 5000 fold expansion of the antigen-specific cells during the 10 day culture. To ensure that CD4$^+$CD25$^+$ Tregs retained regulatory activity after expansion with peptide-I-A$^{g7}$ coated beads, suppression assays were performed using freshly isolated CD4$^+$CD25$^-$ BDC2.5 Tg$^+$ responder cells in combination with a titration of expanded CD4$^+$CD25$^+$ BDC2.5 Tg$^+$ Tregs. Expanded CD4$^+$CD25$^+$ BDC2.5 Tregs efficiently suppressed the CD4$^+$CD25$^-$ T cell response in a dose dependent manner in cultures stimulated with the BDC2.5 mimotope peptide 1040-31. Furthermore, suppressive activity was not lost after multiple rounds of in vitro stimulation. CD4$^+$CD25$^+$ BDC2.5 Tg$^+$ cells, initially seeded at 0.001% and expanded to 50% after two rounds of stimulation with peptide-I-A$^{g7}$ beads, suppressed CD4$^+$CD25$^-$ BDC2.5 Tg$^+$ cells stimulated with the p31 peptide. Thus, even when the antigen-specific BDC2.5 TCR Tg$^+$ Treg cells represented an extremely small percentage of the total polyclonal Treg population, the procedure resulted in a large expansion of antigen-specific Tregs that retained suppressive function.

We next applied this approach to the expansion of antigen-specific CD4$^+$CD25$^+$ Tregs from conventional NOD mice. CD4$^+$CD25$^+$CD62L$^+$ cells from NOD mice were cultured with p31-I-A$^{g7}$ beads as described in Material and Methods (25). Over a 7 to 14 day period the total population typically expanded 1 to 10 fold compared to the initial cell input. Flow cytometry analysis demonstrated that after expansion with the p31-I-A$^{g7}$ beads up to 10% of CD4$^+$CD25$^+$ cells stained positive for the p31-I-A$^{g7}$ multimer while CD4$^+$CD25$^+$ cells expanded with anti-CD3-coated beads did not stain positive for p31-I-A$^{g7}$ above background levels. Under the same culture conditions CD4$^+$CD25$^-$CD62L$^+$ T effectors (Teff) typically expanded 10 fold with 40 to 50% staining positive for the p31-I-A$^{g7}$ multimer. However, the multimer staining was clearly an underestimate of the p31-I-A$^{g7}$-reactive Treg cells based on in vitro proliferation assays. Expanded Treg cells were labeled with carboxyfluorescein succinimidyl ester (CFSE) and cultured with the p31 peptide or control ovalbumin (OVA) peptide in the presence of antigen presenting cells (APC) and anti-CD28. The results of CFSE dilution assays showed that over 50% of p31-I-A$^{g7}$ cultured Tregs entered into cell cycle compared to the background proliferation of 14% in ovalbumin-stimulated cultures. The high degree of background proliferation seen with the OVA peptide may reflect that the cultures were not 100% resting due to the continual presence of beads in the culture. Prior to stimulation, this same cell population had only 6.4% p31-reactive cells when analyzed by flow cytometry for p31-I-A$^{g7}$ multimer binding. These results indicate that T cells with low avidity are poorly detected by multimer staining and may reflect the fact that the TCR are specific for endogenous antigens that are not precisely the same as the p31 mimotope of the BDC2.5 specificity. To explore the validity of this interpretation we examined the Vβ repertoire of the p31-I-A$^{g7}$-expanded T cells. The BDC2.5 T cell receptor expresses a TCRβ derived from the Vβ4 family (26). However, when p31-I-A$^{g7}$ expanded Treg and Teff cells were co-stained with p31-I-A$^{g7}$ multimers and different TCR Vβ reagents neither population was monoclonal. Instead, both populations showed a broad repertoire with several Vβ populations represented. Interestingly, although there were a significant number of Vβ4$^+$ p31-I-A$^{g7}$ multimer$^+$ T cells in the Treg culture, other TCR Vβ were also present in significant numbers, for instance, Vβ2 and Vβ12 which accounted for 10.2 and 13.7% of the p31-I-A$^{g7}$ multimer$^+$ Tregs, respectively, in this representative culture. TCR Vβ4$^+$ T cells were generally present in the p31-I-A$^{g7}$ multimer$^+$ T effector population but at a lower percentage. Together these results indicate that a broad repertoire of Treg and Teff cells reactive against the islet peptide-mimic are resident in conventional NOD mice. The results also indicate that the islet peptide-mimic-reactive Treg repertoire is not identical to the islet peptide-mimic-reactive Teff repertoire.

As observed previously for anti-CD3-expanded cultures, peptide-I-A$^{g7}$-expanded Tregs retained the CD4$^+$CD25$^+$CD62L$^+$ phenotype throughout the culture period in contrast to CD4$^+$CD25$^-$CD62L$^+$ cells that were cultured in a similar manner. CD4$^+$CD25$^-$CD62L$^+$ cells became CD25$^{high}$ upon activation but after the initial activation slightly down regulated CD25 compared to p31-I-A$^{g7}$ reactive Treg cells. The majority of p31-I-A$^{g7}$-reactive T effector cells down regulated CD62L during the culture period. We also examined the expanded Treg and Teff cells for the expression of the Treg lineage marker Foxp3 using quantitative real time PCR. To ensure that p31-I-A$^{g7}$ reactive cells were analyzed, p31-I-A$^{g7}$-expanded Tregs were sorted into p31-I-A$^{g7}$-multimer positive and negative populations by fluorescent activated cell sorting (FACS) prior to analysis. In a representative experiment expanded p31-I-A$^{g7}$-multimer$^+$ Tregs expressed approximately 3000 fold more Foxp3 relative to expanded p31-I-A$^{g7}$-multimer positive T effectors. Expanded p31-I-A$^{g7}$ Tregs also expressed the quintessential Treg surface markers CTLA-4, ICOS, and GITR when analyzed by flow cytometry. We next examined cytokine secretion by p31-I-A$^{g7}$ expanded Tregs upon challenge with antigen. Consistent with data reported previously for Tregs, p31-I-A$^{g7}$-expanded Tregs expressed low levels of the proinflammatory cytokines IL-2. IL-4, and IFNγ and expressed high levels of the anti-inflammatory cytokine IL-10.

Previous studies have shown that CD4$^+$CD25$^+$ Tregs can suppress proliferation of CD4$^+$ effectors in vitro and that the suppressive effect is dependent on stimulation of CD4$^+$CD25$^+$ Tregs through their TCR. Therefore, expanded p31-I-A$^{g7}$ Treg cells were examined for suppressive activity and specificity in vitro. Expanded p31-I-A$^{g7}$ effectively suppressed the proliferation of freshly isolated polyclonal CD4$^+$ T cells and antigen-specific CD4$^+$ BDC2.5 TCR Tg$^+$ mice in a dose-specific manner when cultures were stimulated with the polyclonal activator anti-CD3. More importantly, p31-I-A$^{g7}$ Tregs suppressed the proliferation of BDC2.5 TCR Tg$^+$ CD4$^+$ T cells when the cultures were stimulated with the 1040-31 peptide demonstrating specific suppression by 1040-31 peptide reactive cells in the culture. In contrast, expanded CD4$^+$CD25$^-$ p31-I-A$^{g7}$ Teffs failed to suppress freshly isolated BDC2.5 CD4$^+$ T cells and resulted in augmentation of proliferation. Interestingly, the p31-I-A$^{g7}$ expanded Treg but not Teff cells were anergic to stimulation (both p31 peptide and anti-CD3) in the absence of CD28 co-stimulation consistent with reports for freshly isolated Tregs. To further characterize the antigen specificity of the expanded Tregs, expanded polyclonal Tregs and p31-I-A$^{g7}$ expanded Tregs were assessed for the ability to suppress BDC2.5 TCR Tg+ or Glutamic Acid Decarboxylase peptide 286-specific (GAD286) TCR Tg+ CD4+ cells through either polyclonal T cell activation via anti-CD3 or antigen-specific T cell activation (27). Both polyclonal Tregs and p31-I-A$^{g7}$ expanded Tregs suppressed BDC2.5 TCR Tg+ responders when stimulated with anti-CD3, whereas, only the p31-I-A$^{g7}$ expanded Tregs suppressed cultures stimulated with the BDC2.5 1040-31 peptide. Similarly, both polyclonal Tregs and p31-I-A$^{g7}$-expanded Tregs suppressed the response of GAD286 TCR Tg+ CD4+T cells when stimulated with anti-CD3. However, neither the polyclonal Treg population nor the p31-I-A$^{g7}$-expanded Treg population suppressed GAD286 TCR Tg+ responders when stimulated with the GAD(286-300) peptide. Most significantly, p31-I-A$^{g7}$ expanded Tregs were capable of suppressing GAD286 TCR Tg+ responders when the culture was stimulated with both the GAD(286-300) and the 1040-31 peptide. Collectively these data demonstrate that the suppressive activity of the peptide-I-A$^{g7}$-expanded Tregs is dependent on antigen-specific stimulation through the TCR, although, once stimulated with cognate antigen, p31-I-A$^{g7}$ expanded Tregs are capable of exerting bystander suppression.

We then tested the ability of small numbers of p31-I-A$^{g7}$-expanded Tregs to suppress polyclonal T cell-mediated diabetes in CD28$^-$ NOD mice. CD28$^-$ NOD mice have normal numbers of effector T cells and Th1 responses and undergo an accelerated form of autoimmune diabetes due to a deficiency in Tregs which are dependent on CD28 for homeostasis in the periphery (17, 28). Previous studies have shown that transfer of high numbers (8-20×10$^6$) of polyclonal Tregs can delay or prevent the onset of diabetes (17). Thus, we examined whether p31-I-A$^{g7}$-expanded Tregs transferred into CD28$^{-/-}$ mice could prevent diabetes. Transfer of as few as 1.8 to 2×10$^6$ p31-I-A$^{g7}$ expanded Tregs into 5 to 7-wk-old mice prevented the development of diabetes in 55% of mice for as long as 15 weeks of age. The transferred populations typically contained 10% p31-I-A$^{g7}$ multimer$^+$ cells based on flow cytometry, although the absolute frequency was undoubtedly higher based on the CFSE proliferation assays. Therefore, we estimate that the transferred populations contained 10$^6$ or less antigen-specific Treg cells which is substantially less than similar studies performed with polyclonal NOD Tregs. Thus, the antigen-specific p31-I-A$^{g7}$ expanded cells were highly efficient in protecting the onset of diabetes induced by a fully functional polyclonal T cell response. Moreover, suppression of autoimmunity by the p31-IA$^{g7}$ expanded Tregs was organ-specific as animals that had received p31-I-A$^{g7}$ expanded Tregs and were protected from diabetes at 15 and 16 weeks-of-age displayed a higher degree of lymphocytic infiltration in the salivary and thyroid glands compared to non-treated and polyclonal Treg treated mice that were diabetic and examined at 8-10 weeks-of-age.

In this example, we demonstrate that antigen-specific CD4+CD25+Foxp3+ Tregs reactive to an islet-peptide mimic reside in the periphery of diabetes-susceptible NOD mice. Furthermore, we demonstrate that antigen-specific cells can be selectively expanded in vitro from a polyclonal population and that these expanded Tregs retain phenotypic and functional characteristics of freshly isolated CD4+CD25+Foxp3+ Tregs. We show that in vivo, expanded antigen-specific Tregs are highly efficient at controlling organ-specific autoimmunity. These results support previous studies demonstrating that immune regulation by CD4+CD25+ Tregs is dependent on the antigen specificity of the Tregs and are not consistent with reports suggesting that Tregs function in an antigen non-specific fashion by competing for T cell niches (19, 22, 29).

Our findings provide Treg-based approaches for clinical therapy, which entail expansion of organ-specific Tregs from peripheral blood. Even where small numbers of autoantigen-specific Treg with restricted repertoires are expanded, these cells can be clinically efficacious because of the ability to suppress polyclonal T cell responses either by bystander cytokine production and/or recruitment of endogenous regulatory cells. Many organ-specific antigens have been identified that contribute to autoimmune diseases such as T1D and multiple sclerosis, and currently available human MHC multimer reagents can be employed to expand human organ-specific Tregs for treatment of autoimmune diseases (2).

REFERENCES

1. S. Arif et al., J. Clin. Invest. 113, 451 (2004).
2. N. A. Danke, et al. k, J. Immunol. 172, 5967 (2004).
3. L. Chatenoud, B. Salomon, J. A. Bluestone, Immunol. Rev. 182, 149 (2001).
4. S. Sakaguchi, Annu. Rev. Immunol. 22, 531 (2004).
5. T. A. Chatila et al., J. Clin. Invest. 106, R75 (2000).
6. C. L. Bennett et al., Nature Genet. 27, 20 (2001).
7. M. E. Brunkow et al., Nature Genet. 27, 68 (2001).
8. R. S. Wildin et al., Nature Genet. 27, 18 (2001).
9. J. D. Fontenot, M. A. Gavin, A. Y. Rudensky, Nature Immunol. 4, 330 (2003).
10. R. Khattri, T. Cox, S. A. Yasayko, F. Ramsdell, Nature Immunol. 4, 337 (2003).
11. S. Hori, T. Nomura, S. Sakaguchi, Science 299, 1057 (2003).
12. A. Kukreja et al., J. Clin. Invest. 109, 131 (2002).
13. M. R. Ehrenstein et al., J. Exp. Med. 200, 277 (2004).
14. M. A. Kriegel et al., J. Exp. Med. 199, 1285 (2004).
15. V. Viglietta, et al. J. Exp. Med. 199, 971 (2004).
16. C. Baecher-Allan, D. A. Hafler, J. Exp. Med. 200, 273 (2004).
17. B. Salomon et al., Immunity 12, 431 (2000).
18. S. Gregori, N. Giarratana, S. Smiroldo, L. Adorini, J. Immunol. 171, 4040 (2003).
19. Q. Tang et al., J. Exp. Med. 199, 1455 (2004).
20. J. A. Bluestone, Q. Tang, Proc. Natl. Acad. Sci. U.S.A. 101, 14622 (2004).
21. A. E. Herman, G. J. Freeman, D. Mathis, C. Benoist, J. Exp. Med. 199, 1479 (2004).
22. K. V. Tarbell, et al., J. Exp. Med. 199, 1467 (2004).
23. E. L. Masteller et al., J. Immunol. 171, 5587 (2003).
24. V. Judkowski et al., J. Immunol. 166, 908 (2001).
25. Information on materials and method is available on Science Online.
26. J. D. Katz, B. Wang, K. Haskins, C. Benoist, D. Mathis, Cell 74, 1089 (1993).
27. K. V. Tarbell et al., J. Exp. Med. 196, 481 (2002).
28. Q. Tang et al., J. Immunol. 171, 3348 (2003).
29. T. Barthlott, G. Kassiotis, B. Stockinger, J. Exp. Med. 197, 451 (2003).

Example 3

Clinical Remission of Lupus Nephritis After Adoptive Transfer of Expanded Treg Cells Study size: Total number of subjects: 20; total number of sites 2

Study duration: 12-24 months

Target Population: Patients with lupus nephritis

Rationale: The importance of regulatory T lymphocytes (Treg) in the control of auto immunity is now well-established in a variety of experimental animal models (McHugh et al., The role of suppressor T cells in regulation of immune responses. J Allergy Clin Immunol 10:693-702, 2002). In addition, there are numerous studies suggesting that Treg deficits may be an underlying cause of human autoimmune diseases. Most importantly, the emergence of $CD4^+CD25^+$ regulatory T cells as an essential component of immune homeostasis provides a potential therapeutic opportunity for active immune regulation and long-term tolerance induction. However, Tregs represent only a small percentage (<2%) of human $CD4^+$ T cells, are reduced in number and function in autoimmune humans, and are generally considered to be proliferatively anergic. We have developed a potent method to expand Treg cells from humans. The cells, expanded up to 200-fold in less than 3 weeks, express a classical Treg phenotype ($CD4^+$, $CD25^+$, $CD62L^{hi}$, $GITR^+$, and $FoxP3^+$) and function to suppress T cell effector proliferation and cytokine production.

The present study was designed to test the safety and efficacy of $CD4^+CD25^+$ cells expanded from patients with lupus nephritis. Preliminary data suggested that patients with systemic lupus erythematosus (SLE) demonstrate variability in Treg activity depending on the disease status with high Treg activity during remission and a decline at relapse (Crispin et al., Quantification of regulatory T cells in patients with systemic lupus erythematosus. J Autoimmun 21:273-276, 2003). We sought to determine whether we could identify, select and expand Treg from patients at the time of remission, store those cells by cryopreservation, and reintroduce during relapse. The study was designed to test the safety of such autologous Treg therapy, and to determine the impact of this therapy on disease course and immunologic parameters.

Study Design/Treatment Protocol: The study consists of two phases. In the first phase, we expand Treg from 5 patients with active lupus nephritis and 5 patients with a history of lupus nephritis in remission (off immunosuppressive therapy). This phase demonstrates the relative feasibility of expanding Treg from patients with active and inactive disease, and documents the functional capacity of the expanded cells.

The second phase is an open-label trial of Treg infusion in patients with active lupus nephritis using two different design protocols. In the first protocol, we expand functional Treg from patients with active disease, then these patients will immediately be the recipients of their own expanded cells. Entry criteria include, in addition to active lupus nephritis, the presence of anti-dsDNA antibodies and hypocomplementemia. The entry criteria also include appropriate foundation therapy for nephritis (e.g., prednisone, mycophenolate mofetil, azathioprine, etc.). However, cyclophosphamide (CTX) therapy was an exclusion based on concern that CTX may be more likely to interfere with the effects of Treg. The primary endpoint is the safety of the autologous transfer, assessed by monitoring general clinical parameters and disease activity. The secondary endpoints (disease activity, serology, and mechanistic studies) are measured at 30, 60, 90, 180, and 365 days post-treatment.

The second protocol is applied where sufficient Treg cannot be recovered from patients with active lupus nephritis. Here, the cells are recovered from patients during periods of disease remission, expanded ex vivo, and then frozen in preparation for infusion at the time of relapse. Other than a larger patient pool and time period, the design of this trial paralleled the design described above.

The methods and materials parallel those described below for our Phase I study of adoptive cell transfer in diabetes patients. Our selected FDA-approved anti-CD3/anti-CD28 coated beads and the specified monoclonal antibodies are available from Xcyte Therapies and Becton Dickinson, respectively. We have scaled the sorting and expansion procedure to expand and cryopreserve about $10^9$ Treg from individual patients.

Primary Outcome: Safety

Secondary Outcomes: 1) Renal function, assessed by creatinine, proteinuria, and urinary sediment; 2) Lupus serology, assessed by anti-dsDNA antibodies and complement; 3) disease activity indices, assessed by SLEDAI and/or BILAG, and by patient global assessment; and 4) Mechanistic studies.

Mechanistic Studies: 1) Measurement of anti-dsDNA and complement; 2) Assessment of the frequency of autoantibody-producing B cells; 3) Phenotypic analysis of circulating lymphocytes to detect Treg phenotype; 4) Assessment of Treg activity; and 5) ELISPOT for Th1 and Treg cytokines.

Interpretation. This study demonstrates that Treg cells derived from patients with lupus nephritis have no untoward effects on health or disease progression in the patients, and that adoptive transfer therapy improves renal function in these patients.

Example 4

Clinical Remission of Diabetes Mellitus after Adoptive Transfer of Expanded Treg Cells This trial demonstrates clinical remission of diabetes mellitus after adoptive transfer of expanded Treg cells. Our study lymphocyte collection and infusion protocols were adapted from Rapoport, et al.: Molecular remission of CML after autotransplantation followed by adoptive transfer of costimulated autologous T cells. Bone Marrow Transplant (Epub ahead of print, Oct. 27, 2004).

Patient eligibility and enrollment. We required that prior written and informed consent be obtained from all patients, in accordance with the Institutional Review Board guidelines. Patients are required to have diabetes mellitus based on characteristic clinical and laboratory features. Adequate renal, cardiac, pulmonary, and hepatic functions are required, and patients may not have active infections or HIV seropositivity.

Steady-state lymphocyte collection. Patients first undergo a steady-state leukapheresis using an automated cell separator (Cobe Spectra cell collector or equivalent). Approximately 20-30 l of blood is processed through a large bore catheter, to obtain about $1.5 \times 10^8$ mononuclear cells per kg body weight. These cells are cryopreserved for later expansion in our anti-CD3/anti-CD28 culture system.

Ex vivo costimulation and expansion of T-lymphocytes. T cells are cultured, as specified, in an FDA-approved investigational new drug application. Around day 0 of the autotransplantation phase, the cryopreserved mononuclear cells are thawed and washed three times in PBS with 1% human serum albumin. If not performed at the time of initial cryopreservation, the mononuclear cells are monocyte-depleted using magnetic beads in a closed system. The cells are then seeded into gas-permeable flasks (Baxter Oncology, Deerfield, Ill., USA) containing X-VIVO supplemented with 5% pooled AB serum. Paramagnetic beads with immobilized anti-CD3 (OKT3) and anti-CD28 (9.3) monoclonal antibodies are added at a 2:1 bead:CD3+ cell ratio, and the IL-2 (1000 IU/ml) supplemented cultures maintained for up to 14 days prior to harvest and preparation for infusion (supra). The cells are counted daily and fresh medium supplemented with IL-2 at 1000 IU/ml is added to maintain the cells at a density of $0.75-2 \times 10^6$/ml. After completion of cell culture, the magnetic beads are removed using a Baxter Fenwal Maxsep magnetic cell separation device. After removal of the beads, the cells are washed, concentrated and resuspended in 100-250 ml of Plasmalyte A containing 1% human serum albumin, using the Baxter Fenwal Harvester System.

Reinfusion of ex vivo expanded T cells. Before release, all the harvested products are required to meet the criteria for cell viability (70%), sterility (negative cultures for bacteria and fungi, negative endotoxin assay), and bead contamination (<100 beads/$3\times10^6$ cells). The harvested cells are transported by courier from the cell production facility to the patient and infused on the same day. The cells are infused over 20-60 min without a leukocyte filter. Patients may be routinely premedicated with acetaminophen and diphenhydramine.

Example 5

Clinical Remission of Diabetes Mellitus after Adoptive Transfer of Expanded Treg Cells This trial demonstrates clinical remission of diabetes mellitus after adoptive transfer of expanded Treg cells. Our study lymphocyte collection and infusion protocols were adapted from Rapoport, et al.: Molecular remission of CML after autotransplantation followed by adoptive transfer of costimulated autologous T cells. Bone Marrow Transplant (Epub ahead of print, Oct. 27, 2004).

Patient eligibility and enrollment. We required that prior written and informed consent be obtained from all patients, in accordance with the Institutional Review Board guidelines. Patients are required to have diabetes mellitus based on characteristic clinical and laboratory features. Adequate renal, cardiac, pulmonary, and hepatic functions are required, and patients may not have active infections or HIV seropositivity.

Steady-state lymphocyte collection. Patients first undergo a steady-state leukapheresis using an automated cell separator (Cobe Spectra cell collector or equivalent). Approximately 20-30 l of blood is processed through a large bore catheter, to obtain about $1.5\times10^8$ mononuclear cells per kg body weight. These cells are cryopreserved for later expansion in our MHC class II molecule/peptide complex—costimulatory agent culture system.

Ex vivo costimulation and expansion of T-lymphocytes. T cells are cultured, as specified, in an FDA-approved investigational new drug application. Around day 0 of the autotransplantation phase, the cryopreserved mononuclear cells are thawed and washed three times in PBS with 1% human serum albumin. If not performed at the time of initial cryopreservation, the mononuclear cells are monocyte-depleted using magnetic beads in a closed system. The cells are then seeded into gas-permeable flasks (Baxter Oncology, Deerfield, Ill., USA) containing X-VIVO supplemented with 5% pooled AB serum. Paramagnetic beads with immobilized MHC Complex type II DQ0602/insulinB peptide (aa5-15) and anti-CD28 (9.3) monoclonal antibodies are added at a 2:1 bead:CD3+ cell ratio, and the IL-2 (1000 IU/ml) supplemented cultures maintained for up to 14 days prior to harvest and preparation for infusion (supra). The cells are counted daily and fresh medium supplemented with IL-2 at 1000 IU/ml is added to maintain the cells at a density of $0.75\text{-}2\times10^6$/ml. After completion of cell culture, the magnetic beads are removed using a Baxter Fenwal Maxsep magnetic cell separation device. After removal of the beads, the cells are washed, concentrated and resuspended in 100-250 ml of Plasmalyte A containing 1% human serum albumin, using the Baxter Fenwal Harvester System.

Reinfusion of ex vivo expanded T cells. Before release, all the harvested products are required to meet the criteria for cell viability (70%), sterility (negative cultures for bacteria and fungi, negative endotoxin assay), and bead contamination (<100 beads/$3\times10^6$ cells). The harvested cells are transported by courier from the cell production facility to the patient and infused on the same day. The cells are infused over 20-60 min without a leukocyte filter. Patients may be routinely premedicated with acetaminophen and diphenhydramine.

The foregoing descriptions of particular embodiments and examples are offered by way of illustration and not by way of limitation. Unless contraindicated or noted otherwise, in these descriptions and throughout this specification, the terms "a" and "an" mean one or more, the term "or" means and/or. All publications and patent applications cited in this specification and all publications cited therein are herein incorporated by reference as if each individual publication were specifically and individually indicated to be incorporated by reference. Although the foregoing invention has been described in some detail by way of illustration and example for purposes of clarity of understanding, it will be readily apparent to those of ordinary skill in the art in light of the teachings of this invention that certain changes and modifications may be made thereto without departing from the spirit or scope of the appended claims.

TABLE A

| Autoimmune disease | Autoantigen | MHC class II molecule/peptide(s) bound |
|---|---|---|
| Lupus erythematosus | giantin<br>golgin-245/p230<br>golgin-160/GCP170<br>golgin-95/GM130<br>golgin-97<br>golgin-67<br>transferrin | 119 - VVKKGTDFQLNQLEGKK<br>(SEQ ID NO:2)<br>119 - VVKKGTDFQLNQLGKK<br>(SEQ ID NO:3)<br>[see Freed et al., J. Immunol. (2000)<br>164: 4697-4705 (ref 1)] |
| | $A_\beta^\kappa$(37-51 major;<br>37-52 minor) | YVRFDSDVGEYRAVTE<br>(SEQ ID NO:4) (ref 1) |
| | Lysozyme c (48-63) | GDQSTDYGIFQINSRY<br>(SEQ ID NO:5) (ref 1) |

TABLE A-continued

| Autoimmune disease | Autoantigen | MHC class II molecule/peptide(s) bound |
|---|---|---|
| | nucleoporin NUP 155 (120-) | RQVRFYSGVIEL (SEQ ID NO:6) (ref 1) |
| | Saposin D (37-) | LPDPYQKQCDDFVAE (SEQ ID NO:7) (ref 1) |
| | 26S proteasome p112 (224-) | IFLDDPQAVSDVL (SEQ ID NO:8) (ref 1) |
| | 14-3-3 protein β, δ ζ, θ, or τ (95-) | KTAFDEAIAELD (SEQ ID NO:9) (ref 1) |
| | $A^{78}{}_{\beta}$(143-) (110-) | STQLIRNGDWTFQVLVMLEM (SEQ ID NO:10) HHNTLVCSVTDFYPAKIKVR (SEQ ID NO:11) (ref 1) |
| | Ig γ1-chain (141-) | SMVTLGCLVKGYFPEPVTVT (SEQ ID NO.12) (ref 1) |
| Thrombocytopenic purpura | GPIIb/IIIa | HLA-DR (Kuwana et al., J Clin Invest. 1998 Oct. 1;102(7): 1393-402) |
| | platelet integrin | |
| Goodpasture's syndrome | human glomerular basement membrane | |
| Graves disease | thyroglobulin | |
| | thyroperoxidase | |
| | sodium-iodide symporter | |
| | TSH receptor | |
| Type I diabetes mellitus | Insulin, proinsulin | DQ0601/insulin B aa5-15 aa1-15: FVNQHLCGSHLVEAL (SEQ ID NO: 13) (see Ettinger and Kwok, J Immunol. 1998 Mar 1;160(5):2365-73) HLA-DR3 |
| | glutamic acid decarboxylase (GAD65) | HLA-DR4 (DRB1*0401)/271-285 (PRLIAFTSEHSHFSL) (SEQ ID NO:14) 116-130 (NILLQYVVKSFDRST) (SEQ ID NO:15); HLA-DR4 (DRA1*0101)/356-370 (KYKIWMHVDAAWGGG) (SEQ ID NO:16), 376-390 (KHKWKLNGVERANSV) (SEQ ID NO:17), 481-495 (LYNIIKNREGYEMVF) (SEQ ID NO:18), 511-525 (PSLRVLEDNEERMSR) (SEQ ID NO:19), 546-560 (SYQPLGDKVNFFRMV) (SEQ ID NO:20), 556-570 (FFRMVISNPAATHQD) (SEQ ID NO:21), and 566-580 (ATHQDIDFLIEEIER) (SEQ ID NO:22); HLA-DQ8/206-220 (TYEIAPVFVLLEYVT) (SEQ ID NO:23) (see Peng, Y. Chin Med J 2001;114(10):229-242) |
| | tyrosine phosphatase IA-2 | |
| | tyrosine phosphatase 2b | |

TABLE A-continued

| Autoimmune disease | Autoantigen | MHC class II molecule/peptide(s) bound |
|---|---|---|
| | IGRP<br>Human protein:<br>Q9UN79 - SOX-13<br>protein (Type 1<br>diabetes autoantigen<br>ICA12) (Islet cell<br>antigen 12).<br><br>ICA69 | |
| Myasthenia gravis | Gravin<br>muscle nicotinic<br>acetylcholine<br>receptor (AChR) | 121-136 (PAIFKSYCEIIVTHFP)<br>(SEQ ID NO:24)<br>129-145 (EIIVTHFPFDEQNCSMK)<br>(SEQ ID NO:25) [see J Immunol<br>159(3): 1570-7]<br>p195-212 (DTPYLDITYHFVMQRLPL)<br>(SEQ ID NO:26)<br>[see Scand J Immun. 44(5):512-21] |
| Pemphigus vulgaris | desmoglein 1,<br>desmoglein 3,<br>Human desmocollin<br>1 (Dsc1) | |
| bullous pemphigoid | BP 180 | |
| Autoimmune<br>hepatitis | Formiminotransferase<br>cyclodeaminase | |
| Autoimmune atrophic<br>corpus gastritis | parietal cell H, K-<br>adenosine<br>triphosphatase<br>(ATPase) | |
| Addison's disease | CYP21<br><br>CYP17<br><br>CYP11A1 | |
| Rheumatoid arthritis | endoplasmic<br>reticulum molecular<br>chaperone<br>immunoglobulin<br>binding protein (BiP) | |
| | human cartilage<br>glycoprotein-39<br>(YKL40) | HLA-DR4 (DRB1*0401)/aa259-271<br>(PTFGRSFTLASSE) (SEQ ID NO:27)<br>(see Vos et al, Rheumatology (2000)<br>39:1326-1331) |
| | type II collagen | |
| | glucose-6-phosphate<br>isomerase | |
| Multiple sclerosis | alpha β-Crystallin | DRB1*1501 |
| | myelin<br>oligodendrocyte<br>glycoprotein (MOG) | HLA-DR4 (DRB1*0401)/97-108<br>(TCFFRDHSYQEE) (SEQ ID NO:28)<br>(see Forsthuber et al, J Immunol. 2001<br>Dec 15;167(12):7119-25) |
| | Myelin basic protein<br>(MBP) | 111-119 (SLSRFSWGA) (SEQ ID<br>NO:29) and 87-95 (VVHFFKNIV)<br>(SEQ ID NO:30 presented in HLA-A2<br>and HLA-A24<br>[see JI, 172(8): 5120-7] |
| | X2MBP | |

TABLE A-continued

| Autoimmune disease | Autoantigen | MHC class II molecule/peptide(s) bound |
|---|---|---|
| Psoriasis | Cytokeratin 17 | |
| | cutaneous lymphocyte antigen (CLA) | |
| Autoimmune hemolytic anemia | anion channel protein band 3 | 861-874 (CLAVLWVVKSTPAS) (SEQ ID NO:31) [see Blood 15;102(10):3800-6] |
| Uveitis | S-antigen | 341-354 (FLGELTSSEVATEV) (SEQ ID NO:32) see Int. Immun., 15(8):927-935 |
| | interphotoreceptor retinoid-binding protein (IRBP) | |
| | HLA-B(B27PD) | 125-138 ALNEDLSSQTAADT (SEQ ID NO:1) [see Int. Immun. 15(8):927-935 |

What is claimed is:

1. A method of adoptive cellular immunotherapy, the method comprising the steps of:
    extracting a mixed population of T cells from a patient diagnosed with Type I diabetes or autoimmune diabetes and presenting an indication of impaired glucose homoeostasis selected from fasting plasma glucose (FPG), post-prandial glucose (PPG), and glucose tolerance (GTT);
    isolating from the population a subpopulation comprising >98% CD4$^+$CD25$^+$ T cells (Treg cells) by negative and positive immuno-selection and cell sorting;
    expanding the Treg cells of the subpopulation at least 100-fold by contacting the subpopulation with effective amounts of (i) a MHC-peptide multimer ligand for TCR/CD3 wherein the peptide is a diabetes-associated autoantigen peptide and the diabetes-associated autoantigen is selected from glutamic acid decarboxylase (GAD), an islet cell autoantigen (ICA) and insulin, (ii) a multivalent antibody specific for CD28; and (iii) IL-2, wherein the effective amount of IL-2 is 200 to 2500 IU IL-2/ml, to obtain ex vivo expanded Treg cells;
    introducing into the patient $10^7$ to $10^{11}$ of the ex vivo expanded Treg cells; and
    detecting a resultant improvement in the impaired glucose homoeostasis.

2. The method of claim 1, wherein the improvement is selected from an FPG of 110 mg/dL or less, a 2-hour PPG of 140 mg/dL or less, and a GTT of 140 mg/dL or less 2 hours after a 75-g glucose load.

3. The method of claim 2, wherein the diabetes-associated autoantigen is insulin, and introducing step introduces into the patient $10^7$ to $10^9$ of the ex vivo expanded Treg cells.

4. The method of claim 3, wherein the anti-CD28 antibodies are immobilized on paramagnetic beads provided in a Treg cell:bead ratio of between 1:1 and 1:2.

5. The method of claim 1, wherein the introducing step introduces into the patient $10^7$ to $10^9$ of the ex vivo expanded Treg cells.

6. The method of claim 1, wherein the diabetes-associated autoantigen is insulin, and introducing step introduces into the patient $10^7$ to $10^9$ of the ex vivo expanded Treg cells.

7. The method of claim 6, wherein the anti-CD28 antibodies are immobilized on paramagnetic beads provided in a Treg cell:bead ratio of between 1:1 and 1:2.

8. The method of claim 1, wherein the effective amount of IL-2 is 500 to 2500 IU IL-2/ml.

9. The method of claim 1, wherein the effective amount of IL-2 is 1000 to 2000 IU IL-2/ml.

* * * * *

UNITED STATES PATENT AND TRADEMARK OFFICE
CERTIFICATE OF CORRECTION

PATENT NO. : 7,722,862 B2  Page 1 of 1
APPLICATION NO. : 11/473959
DATED : May 25, 2010
INVENTOR(S) : Bluestone et al.

It is certified that error appears in the above-identified patent and that said Letters Patent is hereby corrected as shown below:

On the Title Page:
On Title Page, under OTHER PUBLICATIONS, in Item (56), in the Dieckmann, D., et al. reference, line 6 of the second column, please delete "$CD4^{30}$" and insert --$CD4^{+}$--.

On Title Page, under OTHER PUBLICATIONS, in Item (56), in the Butterfield et al. reference, line 31 of the second column, please insert --"-- before "T-Cell.".

On Title Page, under OTHER PUBLICATIONS, in Item (56), in the Butterfield et al. reference, line 32 of the second column, please delete "n Patients" and insert --in Patients--.

On Title Page, under OTHER PUBLICATIONS, in Item (56), in the Butterfield et al. reference, line 33 of the second column, please insert --"-- after "Hepatocellular Cancer,".

In the Specification:
In the ACKNOWLEDGEMENT OF GOVERNMENT SUPPORT section, column 1, line 8, please delete "A146643" and insert --AI46643 and NIH Grant DK07418--.

In the ACKNOWLEDGEMENT OF GOVERNMENT SUPPORT section, column 1, line 8, please delete "The U.S. government may have rights in any patent issuing on this application" and insert --The U.S. government has certain rights in any patent issuing on this application--.

Signed and Sealed this

Twenty-sixth Day of October, 2010

David J. Kappos
*Director of the United States Patent and Trademark Office*